(12) United States Patent
Asada et al.

(10) Patent No.: US 9,314,546 B2
(45) Date of Patent: Apr. 19, 2016

(54) ADHESIVE COMPOSITION FOR SOFT TISSUES, ADHESIVE COMPOSITION FOR WOUND DRESSING OR WOUND DRESSING COMPOSITION

(75) Inventors: Noriaki Asada, Mobara (JP); Shinya Aoki, Ichihara (JP); Hiroshi Naruse, Chiba (JP); Shoichi Miyakoshi, Sagamihara (JP); Masami Arata, Moriyama (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 13/508,009

(22) PCT Filed: Nov. 18, 2010

(86) PCT No.: PCT/JP2010/070546
§ 371 (c)(1),
(2), (4) Date: May 3, 2012

(87) PCT Pub. No.: WO2011/062214
PCT Pub. Date: May 26, 2011

(65) Prior Publication Data
US 2012/0219544 A1    Aug. 30, 2012

(30) Foreign Application Priority Data

Nov. 20, 2009  (JP) .................................. 2009-265647
Nov. 20, 2009  (JP) .................................. 2009-265649

(51) Int. Cl.
| | | |
|---|---|---|
| *A61L 24/00* | (2006.01) | |
| *A61L 15/58* | (2006.01) | |
| *A61L 15/00* | (2006.01) | |
| *A61L 15/44* | (2006.01) | |
| *A61L 26/00* | (2006.01) | |
| *C08L 33/06* | (2006.01) | |
| *A61L 24/04* | (2006.01) | |

(52) U.S. Cl.
CPC ............... *A61L 24/043* (2013.01); *A61L 15/00* (2013.01); *A61L 15/44* (2013.01); *A61L 15/58* (2013.01); *A61L 26/0014* (2013.01)

(58) Field of Classification Search
None
See application file for complete search history.

(56) References Cited

U.S. PATENT DOCUMENTS

| | | | |
|---|---|---|---|
| 5,264,215 A | 11/1993 | Nakabayashi et al. | |
| 5,459,177 A | 10/1995 | Miyakoshi et al. | |
| 5,461,124 A | 10/1995 | Ritter et al. | |
| 5,530,038 A | 6/1996 | Yamamoto et al. | |
| 5,981,621 A | 11/1999 | Clark et al. | |
| 6,051,626 A | 4/2000 | Zeng et al. | |
| 6,475,502 B1 * | 11/2002 | Lee et al. ........................ | 424/405 |
| 2005/0143827 A1 | 6/2005 | Globerman et al. | |
| 2005/0215660 A1 | 9/2005 | Tomikawa et al. | |
| 2008/0171841 A1 | 7/2008 | Zeng et al. | |

FOREIGN PATENT DOCUMENTS

| | | |
|---|---|---|
| EP | 0252603 A3 | 1/1988 |
| JP | 07-024051 A | 1/1995 |
| JP | 8-99815 A | 4/1996 |
| JP | 9-110913 A | 4/1997 |
| JP | 2005-015435 A | 1/2005 |
| JP | 2005-200342 A | 7/2005 |
| JP | 2006-051121 A | 2/2006 |
| JP | 2007-061658 | 3/2007 |
| JP | 2008-531109 A | 8/2008 |
| WO | WO 03/082931 A1 | 10/2003 |
| WO | WO 2005/067866 A1 | 7/2005 |
| WO | WO 2006/090379 A2 | 8/2006 |

OTHER PUBLICATIONS

International Search Report (PCT/ISA/210) issued on Dec. 21, 2010, by the Japanese Patent Office as the International Searching Authority for International Application No. PCT/JP2010/070546.

Kosuge et al., "Influence of PMMA Power on Properties of MMA-TBB Resin Cement" The Japanese Society for Dental Materials and Devices (JSDMD), 1999, vol. 18, No. 5, pp. 347-351.

Kosuge, "Influence of PMMA Power on Properties of MMA-TBB Resin Cement" The Japanese Society for Dental Materials and Devices (JSDMD), 2000, vol. 19, No. 1, pp. 92-101.

Office Action issued on Sep. 17, 2013, by the Japanese Patent Office in corresponding Japanese Patent Application No. 2011-541945. (3 pages).

Extended European Search Report issued on Apr. 11, 2014, by the European Patent Office, in corresponding European Patent Application No. 10831607.6 (7 pages).

(Continued)

*Primary Examiner* — David J Blanchard
*Assistant Examiner* — Sarah Chickos
(74) *Attorney, Agent, or Firm* — Buchanan, Ingersoll & Rooney PC

(57) ABSTRACT

The adhesive composition for soft tissues, the adhesive composition for wound dressing or the wound dressing agent composition of the present invention is an adhesive composition for soft tissues, an adhesive composition for wound dressing or a wound dressing agent composition, comprising a monomer (A), a polymer (B) and a polymerization initiator composition (C) containing an organoboron compound, and is characterized by having a viscosity of 0.4 to 75,000 cp within 30 seconds after mixing of the components (A), (B) and (C). The composition of the present invention not only has low toxicity, low harmfulness and high adhesive strength but also is excellent in workability during application and is capable of forming films of excellent properties.

19 Claims, 2 Drawing Sheets

(56) References Cited

OTHER PUBLICATIONS

Y. Tsuchiya et al., "Effect of the Dental Adhesive, 4-META/MMA-TBB Resin, on Adhesion and Keratinization of Regenerating Oral Epithelium", Journal of Periodontal Research, vol. 44, No. 4, Aug. 1, 2009 pp. 496-502.

Notice of Acceptance issued on Jun. 18, 2014, by the Australian Patent Office in corresponding Australian Patent Application No. 2010320137. (3 pages).

Office Action issued in corresponding Chinese Application No. 201080048137.4 on Feb. 27, 2015 (5 pages).

* cited by examiner

← 1 1
← 1 2
← 1 3
← 1 2
← 1 1

← 2 1
← 2 2
← 2 3
← 2 4
← 2 3
← 2 2
← 2 1

US 9,314,546 B2

ADHESIVE COMPOSITION FOR SOFT TISSUES, ADHESIVE COMPOSITION FOR WOUND DRESSING OR WOUND DRESSING COMPOSITION

TECHNICAL FIELD

The present invention relates to an adhesive composition for soft tissues, an adhesive composition for wound dressing or a wound dressing composition.

BACKGROUND ART

As soft tissue adhesives, adhesives for wound dressing or wound dressings, various compositions, e.g., compositions containing cyanoacrylate and compositions using materials derived from organisms, such as compositions containing fibrin and compositions containing albumin, have been studied in the past (see, for example, patent literature 1 and patent literature 2).

The compositions containing cyanoacrylate are excellent in view of high adhesive strength, but they have poor biocompatibility, and there is a serious problem that formaldehyde generated by hydrolysis of cured products of the compositions exhibits high toxicity to organisms and inhibits healing. Particularly in parts that come into direct contact with central nervous system, blood vessels, etc., these compositions cannot be used. Moreover, since the curing time is extremely short, they are sometimes difficult to use.

The compositions containing materials derived from organisms are excellent in that the biocompatibility is high and healing is rarely inhibited, but they have low adhesive strength. Further, when the composition containing fibrin is used as an adhesive or the like, there is a side view that fibrin glue contained in the composition becomes a culture medium for bacteria, so that there is the risk of infection after operation or treatment and there is a fear of harmfulness.

When an adhesive is used for a wound of the skin or a soft tissue, or when a wound dressing is used for a wound, it is a usual way that the components are mixed in advance in a container or the like to prepare a composition and then the composition is applied to the surface of the soft tissue, the wound dressing part or the like, taking into consideration workability, prevention of infection, etc. However, the state of the composition after mixing sometimes has influence on the workability during the application of the composition, that is, for example, if the viscosity of the composition is too high, the composition is hard to apply, or if the viscosity is too low, the composition runs out of the necessary area. Moreover, if properties, such as elasticity and tensile elongation, of a film obtained by polymerization and solidification of the adhesive or the wound dressing are not proper, there sometimes occurs a problem that the film peels off from the skin after application because the skin or the soft tissue is a flexible adherend.

Since acrylic adhesives using an initiator containing an organoboron compound have low toxicity and low harmfulness and have high adhesive strength, development of them to dental applications has been promoted (see, for example, patent literature 3). However, if other medical applications, such as surgical applications, soft tissue adhesion applications and wound dressing applications, are intended, further improvement in handling stability or workability of the composition between mixing of the components and application to the application area has been sometimes required.

CITATION LIST

Patent Literature

Patent literature 1: Japanese Patent Laid-Open Publication No. 061658/2007
Patent literature 2: Japanese Patent Laid-Open Publication No. 051121/2006
Patent literature 3: Japanese Patent Laid-Open Publication No. 110913/1997

SUMMARY OF INVENTION

Technical Problem

It is an object of the present invention to provide a composition which not only has low toxicity, low harmfulness and high adhesive strength but also is excellent in workability during application and is capable of forming a film having properties that are preferable for an adhesive for soft tissues, an adhesive for wound dressing or a wound dressing.

Solution to Problem

In order to solve the above problems, the present inventors have earnestly studied compositions which are preferable as adhesives for soft tissues, adhesives for wound dressing or wound dressings. As a result, they have found that the above problems can be solved by an adhesive composition or a wound dressing composition comprising a monomer, a polymer and a specific polymerization initiator composition and having a viscosity of a specific range after mixing of these components, and they have accomplished the present invention. The adhesive composition for soft tissues, the adhesive composition for wound dressing or the wound dressing composition of the present invention means a composition of materials, with which wounds made in soft tissues, such as skins, muscles, internal organs and blood vessels of organisms, by operations, accidents, etc., i.e., disconnected tissues, are surface-covered to carry out adhesion of skins of the wounds or temporary dressing of the wounds.

That is to say, the adhesive composition for soft tissues, the adhesive composition for wound dressing or the wound dressing composition of the present invention comprises a monomer (A), a polymer (B) and a polymerization initiator composition (C) containing an organoboron compound and has a viscosity of 0.4 to 75,000 cp within 30 seconds after mixing of the components (A), (B) and (C).

The polymer (B) is preferably a polymer mixture which comprises polymer particles (b1) having a weight-average molecular weight of $30 \times 10^4$ to $60 \times 10^4$ and a specific surface area of 1.5 to 4.5 $(m^2/g)$, polymer particles (b2) having a weight-average molecular weight of $5 \times 10^4$ to $20 \times 10^4$ and a specific surface area of 0.51 to 1.2 $(m^2/g)$ and polymer particles (b3) having a weight-average molecular weight of $5 \times 10^4$ to $20 \times 10^4$ and a specific surface area of 0.1 to 0.5 $(m^2/g)$, contains the polymer particles (b1) in an amount of 0 to 98% by weight, and contains the polymer particles (b2) and the polymer particles (b3) in the total amount of not less than 2% by weight based on the total weight of the polymer particles (b1), (b2) and (b3), with the proviso that the total amount of the polymer particles (b1), (b2) and (b3) is 100% by weight.

A film, which is obtained from the above adhesive composition or wound dressing composition, is given 24 hours after the preparation of the composition and has a thickness of not less than 0.1 µm, a length of not less than 25 mm and a width of not less than 2 mm, preferably has a flexural elastic modulus, as measured under the conditions of a test rate of 2 mm/min, of not more than 750 MPa and a tensile elongation, as measured under the conditions of a test rate of 1 mm/min, of not less than 5%.

The adhesive composition or the wound dressing composition may further comprise, for example, a polymerization inhibitor (D), an ultraviolet light absorber, and a plasticizer.

In a preferred embodiment, the content of the polymerization inhibitor (D) in the composition is in the range of 10 to 5000 ppm based on the monomer (A).

The polymerization inhibitor (D) is preferably at least one substance selected from hydroquinone, dibutylhydroquinone, hydroquinone monomethyl ether, 2,6-di-tert-butylphenol, 2,6-di-tert-butyl-p-cresol, catechol, pyrogallol, benzoquinone, 2-hydroxybenzoquinone, p-methoxyphenol, t-butylcatechol, butylated hydroxyanisole, butylated hydroxytoluene and t-butylhydroquinone.

The adhesive composition or the wound dressing composition may further comprise at least one substance selected from:

anti-infectious agents, antibiotics, antibacterial agents, anti-virus agents, analgesics, compositions of analgesics, anorectic drugs, antihelmintic drugs, antiarthritic agents, antiasthmatic drugs, anticonvulsants, antidepressants, antidiuretics, antidiarrheal agents, antihistamine drugs, anti-inflammatory drugs, antimigraine drugs, antiemetic agents, antineoplastic drugs, antiparkinsonian agents, antipruritic drugs, antipsychotics, antipyretic drugs, antispasmodic drugs, anticholinergic agents, sympathomimetic agents, cardiovascular drugs, antiarrhythmic drugs, antihypertensive drugs, diuretics, vasodilators, immunosuppressant drugs, muscle-relaxant drugs, parasympatholytic drugs, stimulants, sedative drugs, tranquilizers, cholinergic agents, chemotherapeutic drugs, radio pharmaceuticals, bone inductive drugs, heparin neutralizer agents of static bladder, procoagulants, hemostatic agents, xanthine derivatives, hormones, proteins of natural origin or proteins synthesized by genetic engineering, polysaccharides, glycoproteins, lipoproteins, oligonucleotides, antibody, antigen, vasopressin, vasopressin analogs, epinephrine, selectin, clot promoting toxicants, plasminogen activating factor inhibitors, platelet activators, synthetic peptides having hemostatic action, and perfumes, such as orange oil, grapefruit oil, lemon oil, lime oil, clove oil, wintergreen oil, peppermint oil, peppermint spirit, banana distillate, cucumber distillate, honey distillate, rose water, menthol, anethole, alkyl salicylate, benzaldehyde, monosodium glutamate, ethylvanillin, thymol and vanillin.

The kit of the present invention used as an adhesive for soft tissues, an adhesive for wound dressing or a wound dressing has members in which the components of the monomer (A), the polymer (B) and the polymerization initiator composition (C) containing an organoboron compound, which are contained in the adhesive composition or the wound dressing composition, are encased in two or more divided groups in an optional combination.

The above kit preferably has constitution in which the monomer (A), the polymer (B) and the polymerization initiator composition (C) are each independently encased, and the monomer (A) is first mixed with the polymerization initiator composition (C) containing an organoboron compound and subsequently mixed with the polymer (B).

When the above kit contains the polymerization inhibitor (D), the kit has members in which the components of the monomer (A), the (meth)acrylate polymer (B), the polymerization initiator composition (C) containing an organoboron compound and the polymerization inhibitor (D), which are contained in the adhesive composition for soft tissues, the adhesive composition for wound dressing or the wound dressing composition, are encased in two or more divided groups in an optional combination.

The kit containing the polymerization inhibitor preferably has constitution in which a mixture of the monomer (A) and the polymerization inhibitor (D), the polymer (B) and the polymerization initiator composition (C) are each independently encased, and the mixture of the monomer (A) and the polymerization inhibitor (D) is first mixed with the polymerization initiator composition (C) containing an organoboron compound and subsequently mixed with the polymer (B).

In the kit, a jig that is used for applying a composition obtained by mixing adhesive components or wound dressing components containing the components (A), (B) and (C) and the components added when needed may be further included.

The jig is, for example, a brush, a fiber ball, a cloth, a sponge ball or a piece of sponge.

In the above kit, an aqueous solution for adhesion pretreatment containing 1 to 15% by weight of citric acid and 1 to 5% by weight of iron(III) chloride may be further contained.

Advantageous Effects of Invention

The adhesive composition for soft tissues, the adhesive composition for wound dressing or the wound dressing composition of the present invention not only has low toxicity, low harmfulness and high adhesive strength but also is excellent in workability during application and is capable of forming a film having properties that are preferable for an adhesive for soft tissues, an adhesive for wound dressing or a wound dressing. When the composition is applied to a wound, the wound can be strongly bonded with the adhesive. Especially when the composition of the invention is applied to a wound of the outer skin, the wound of the outer skin can be joined with the adhesive, and after healing, the adhesive can be naturally separated from the outer skin.

DESCRIPTION OF EMBODIMENTS

Figure 1:
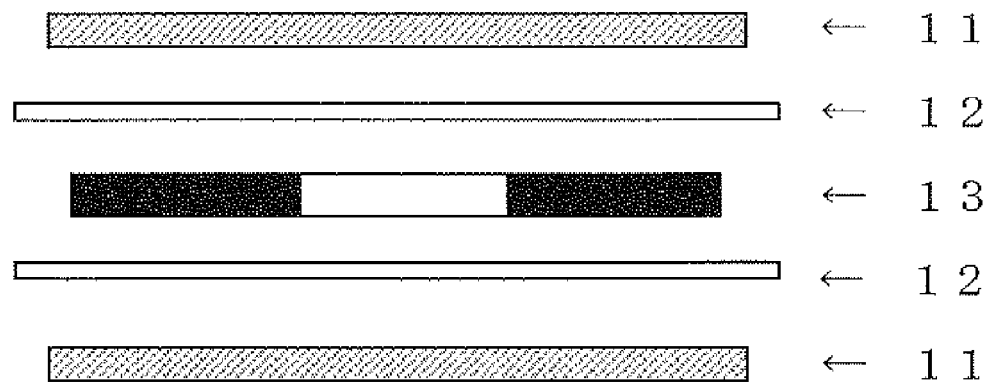
FIG. 1 is a schematic view showing an example of a process for preparing a sample film used in the examples of the present invention.

In the adhesive composition for soft tissues, the adhesive composition for wound dressing or the wound dressing composition of the present invention, a monomer (A) is contained. As the monomer (A), any monomer can be used without specific restriction as long as it can be polymerized by the later-described polymerization initiator composition (C). As the monomer (A), any of a monofunctional monomer and a polyfunctional monomer can be used depending upon the use purpose.

Examples of the monomers (A) include methacrylates, acrylates and other vinyl compounds.

Of such monomers, acrylates and methacrylates are preferable from the viewpoint of relatively low irritation of the human body. Hereinafter, (meth)acrylates may be used to refer to acrylates and methacrylates.

Of the monomers, monomers having an acidic group are preferable from the viewpoint of excellent adhesion properties.

Therefore, use of a combination of a (meth)acrylate (having no acidic group) and a monomer having an acidic group as the monomer (A) is also a preferred embodiment.

Examples of monofunctional (meth)acrylates (having no acidic group) include:

alkyl (meth)acrylates, such as methyl (meth)acrylate, ethyl (meth)acrylate, propyl (meth)acrylate, butyl (meth)acrylate, hexyl (meth)acrylate, 2-ethylhexyl (meth)acrylate, dodecyl (meth)acrylate, lauryl (meth)acrylate, cyclohexyl (meth)acrylate, benzyl (meth)acrylate and isobornyl (meth)acrylate;

hydroxyalkyl esters of (meth)acrylic acid, such as 2-hydroxyethyl (meth)acrylate, 2-hydroxypropyl (meth)acrylate, 3-hydroxypropyl (meth)acrylate, 4-hydroxybutyl (meth)acrylate, 5-hydroxypentyl (meth)acrylate, 6-hydroxyhexyl (meth)acrylate, 1,2-dihydroxypropyl mono(meth)acrylate, 1,3-dihydroxypropyl mono(meth)acrylate and erythritol mono(meth)acrylate;

polyalkylene glycol mono(meth)acrylates, such as diethylene glycol mono(meth)acrylate, triethylene glycol mono (meth)acrylate, polyethylene glycol mono(meth)acrylate and polypropylene glycol mono(meth)acrylate;

(poly)alkylene glycol monoalkyl ether (meth)acrylates, such as ethylene glycol monomethyl ether (meth)acrylate, ethylene glycol monoethyl ether (meth)acrylate, diethylene glycol monomethyl ether (meth)acrylate, triethylene glycol monomethyl ether (meth)acrylate, polyethylene glycol monomethyl ether (meth)acrylate and polypropylene glycol monoalkyl ether (meth)acrylate;

fluoroalkyl esters of (meth)acrylic acid, such as perfluorooctyl (meth)acrylate and hexafluorobutyl (meth)acrylate;

silane compounds having a (meth)acryloxyalkyl group, such as γ-(meth)acryloxypropyltrimethoxysilane and γ-(meth)acryloxypropyltri(trimethylsiloxy)silane; and (meth)acrylates having a heterocyclic ring, such as tetrahydrofurfuryl (meth)acrylate.

Examples of the polyfunctional (meth)acrylates (having no acidic group) include:

poly(meth)acrylates of alkanepolyols, such as ethylene glycol di(meth)acrylate, propyleneglycol di(meth)acrylate, butylene glycol di(meth)acrylate, neopentylglycol di(meth) acrylate, hexylene glycol di(meth)acrylate, trimethylolpropane tri(meth)acrylate and pentaerythritol tetra(meth)acrylate;

polyoxyalkane polyol poly(meth)acrylates, such as diethylene glycol di(meth)acrylate, triethylene glycol di(meth) acrylate, polyethylene glycol di(meth)acrylate, dipropylene glycol di(meth)acrylate, polypropylene glycol di(meth)acrylate, dibutylene glycol di(meth)acrylate and dipentaerythritol hexa(meth)acrylate;

alicyclic or aromatic di(meth)acrylates represented by the following formula (1):

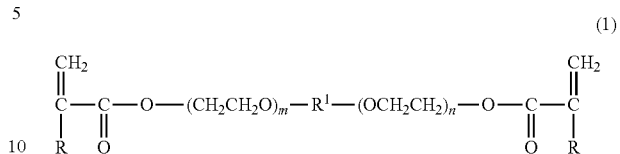

wherein R is a hydrogen atom or a methyl group, m and n are numbers of 0 to 10 which may be the same or different, and $R^1$ is any one of the following:

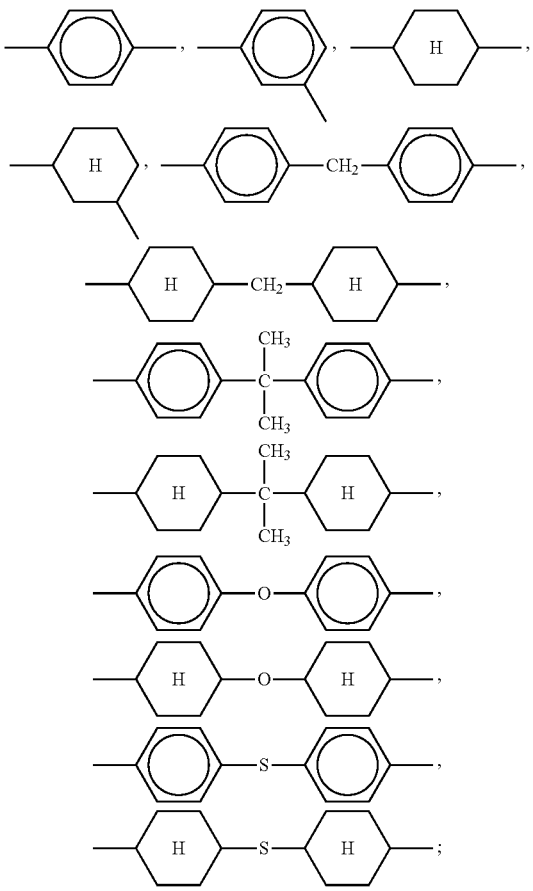

alicyclic or aromatic epoxy di(meth)acrylates represented by the following formula (2):

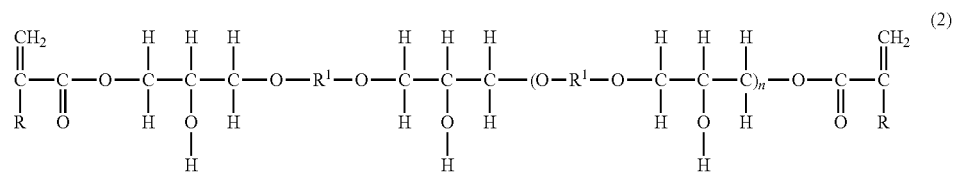

wherein R is a hydrogen atom or a methyl group, n is a number of 0 to 10, and $R^1$ is any one of the following:

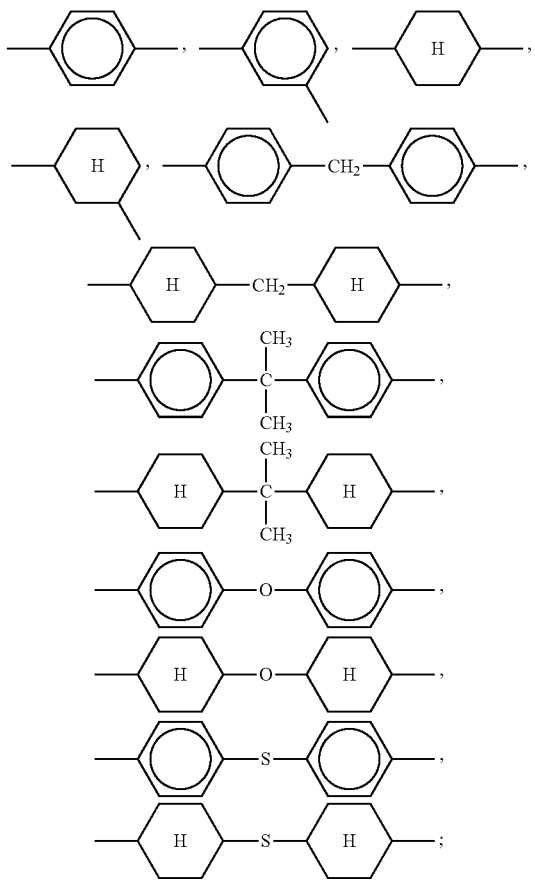

and polyfunctional (meth)acrylates having a urethane bond in a molecule, which are represented by the following formula (3):

wherein R is a hydrogen atom or a methyl group, and $R^2$ is any one of the following:

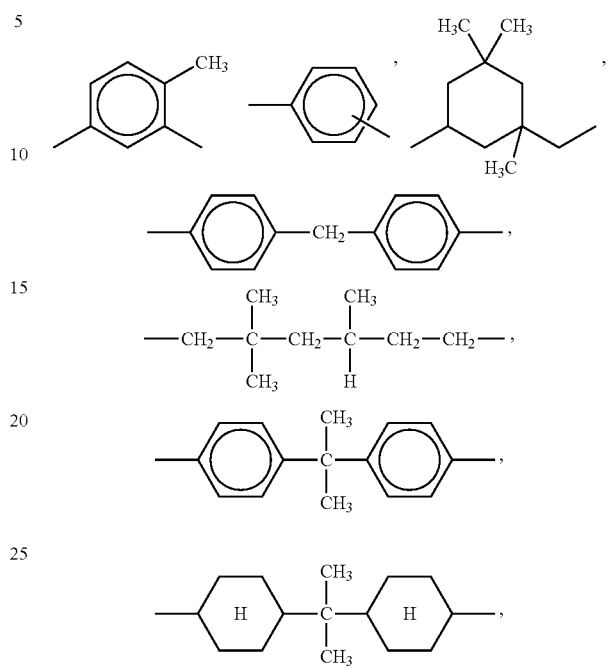

Of these (meth)acrylates, preferred monofunctional (meth)acrylates include:

alkyl (meth)acrylates, such as methyl (meth)acrylate and ethyl (meth)acrylate;

hydroxyalkyl esters of (meth)acrylic acid, such as 2-hydroxyethyl (meth)acrylate, 1,3-dihydroxypropyl mono (meth)acrylate and erythritol mono(meth)acrylate; and polyethylene glycol mono (meth)acrylates, such as triethylene glycol monomethyl ether (meth)acrylate and triethylene glycol mono(meth)acrylate.

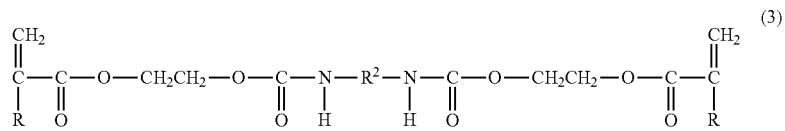

Preferred polyfunctional (meth)acrylates include:

di(meth)acrylates having an ethylene glycol chain in a molecule, such as triethylene glycol di(meth)acrylate and polyethylene glycol di(meth)acrylate;

compounds represented by the following formula (1)-a:

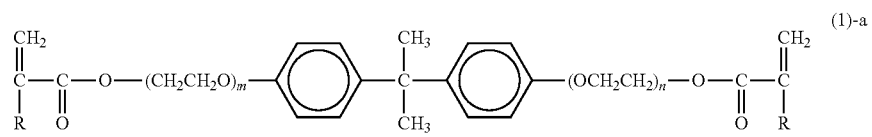

wherein R is a hydrogen atom or a methyl group, and m and n are numbers of 0 to 10 which may be the same or different; compounds represented by the following formula (2)-a:

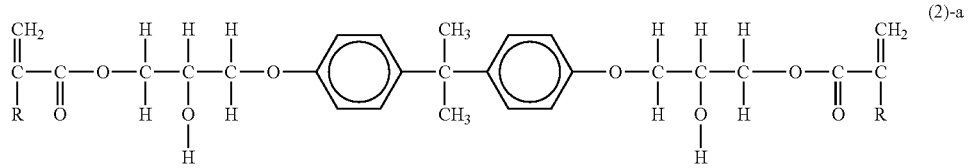

wherein R is a hydrogen atom or a methyl group; and compounds represented by the following formula (3)-a:

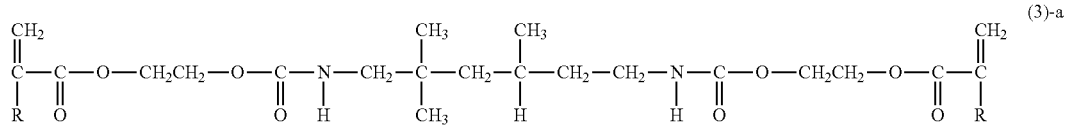

wherein R is a hydrogen atom or a methyl group.

These (meth)acrylates can be used singly or in combination of two or more kinds.

Examples of the monomers having an acidic group include:

monomers having a carboxylic acid group or its anhydride group, such as (meth)acrylic acid and its anhydride, 1,4-di(meth)acryloxyethylpyromellitic acid, 6-(meth)acryloxyethylnaphthalene-1,2,6-tricarboxylic acid, N-(meth)acryloyl-p-aminobenzoic acid, N-(meth)acryloyl-o-aminobenzoic acid, N-(meth)acryloyl-m-aminobenzoic acid, N-(meth)acryloyl-5-aminosalicylic acid, N-(meth)acryloyl-4-aminosalicylic acid, 4-(meth)acryloxyethyltrimellitic acid and its anhydride, 4-(meth)acryloxybutyltrimellitic acid and its anhydride, 4-(meth)acryloxyhexyltrimellitic acid and its anhydride, 4-(meth)acryloxydecyltrimellitic acid and its anhydride, 2-(meth)acryloyloxybenzoic acid, 3-(meth)acryloyloxybenzoic acid, 4-(meth)acryloyloxybenzoic acid, β-(meth)acryloyloxyethyl hydrogensuccinate, β-(meth)acryloyloxyethyl hydrogenmaleate, β-(meth)acryloyloxyethyl hydrogenphthalate, 11-(meth)acryloyloxy-1,1-undecanedicarboxylic acid, and p-vinylbenzoic acid;

monomers having a phosphoric acid group, such as (2-(meth)acryloxyethyl)phosphoric acid, (2-(meth)acryloxyethylphenyl)phosphoric acid and 10-(meth)acryloxydecylphosphoric acid; and monomers having a sulfonic acid group, such as p-styrenesulfonic acid and 2-acrylamido-2-methylpropanesulfonic acid.

Of these monomers having an acidic group, 4-methacryloxyethyltrimellitic acid and its anhydride are preferable.

These monomers having an acidic group can be used singly or in combination of two or more kinds. By the use of these monomers having an acidic group, the adhesive composition for soft tissues, the adhesive composition for wound dressing or the wound dressing composition tends to have more improved adhesion properties.

The monomer having an acidic group is preferably contained in an amount of 1 to 20 parts by weight, more preferably 1 to 10 parts by weight, still more preferably 1 to 8 parts by weight, based on 100 parts by weight of the total amount of the (meth)acrylate (having no acidic group) and the monomer having an acidic group. If the amount thereof is out of the above range, an evil influence is sometimes exerted on the adhesive strength or the biocompatibility.

The amount of the monomer (A) is preferably in the range of 10 to 98.95 parts by weight, more preferably 25 to 89.5 parts by weight, still more preferably 37 to 86 parts by weight, based on 100 parts by weight of the total amount of the monomer (A), the later-described polymer (B) and the later-described polymerization initiator composition (C).

If the amount of the monomer (A) is less than the lower limit of the above range, the viscosity is increased, and application tends to be difficult. If the amount of the monomer (A) exceeds the upper limit of the above range, the adhesive strength is poor, and there is a possibility that the mixture runs out of the desired area to obstruct the treatment.

In some cases, the amount of the monomer (A) is preferably in the range of 5 to 98.95 parts by weight, more preferably 17 to 98.5 parts by weight, still more preferably 20 to 85 parts by weight, particularly preferably 24 to 85 parts by weight, much more preferably 24 to 48 parts by weight, based on 100 parts by weight of the total amount of the monomer (A), the later-described polymer (B) and the later-described polymerization initiator composition (C).

If the amount of the monomer (A) is less than the lower limit of the above range, the viscosity is increased, and operations such as application tend to become difficult. If the amount of the monomer (A) exceeds the upper limit of the above range, adhesive strength and other properties, such as flexural elastic modulus, tensile strength and flexural strength, tend to become poor. Moreover, there is a possibility that the mixture runs out of the desired area to obstruct the treatment.

In the adhesive composition for soft tissues, the adhesive composition for wound dressing or the wound dressing composition of the present invention, a polymer (B) is further contained.

Examples of the polymers (B) include methacrylate polymers, acrylate polymers, styrene-based elastomers, vinyl chloride-based elastomers, olefin-based elastomers, polyester-based elastomers, polyamide-based elastomers, urethane-based elastomers, an ethylene/vinyl acetate copolymer and a silicon polymer. These polymers can be used singly or in combination of two or more kinds.

Of these polymers (B), preferable are methacrylate polymers and acrylate polymers from the viewpoint of homogeneity in the mixing process. The methacrylate polymers and the acrylate polymers are sometimes generically referred to as "(meth)acrylate polymers" hereinafter.

Examples of the (meth)acrylate polymers include:

uncrosslinked polymers, such as polymethyl (meth)acrylate, polyethyl (meth)acrylate, a methyl (meth)acrylate/ethyl (meth)acrylate copolymer, a methyl (meth)acrylate/butyl (meth)acrylate copolymer and a methyl (meth)acrylate/styrene copolymer: and crosslinked polymers, such as a methyl (meth)acrylate/ethylene glycol di(meth)acrylate copolymer, a methyl (meth)acrylate/triethylene glycol di(meth)acrylate copolymer and a copolymer of methyl (meth)acrylate and a butadiene-based monomer.

When the rubbers, such as natural rubbers and synthetic rubbers, and the elastomers, such as thermoplastic elastomers, among the above polymers are used by mixing them with the (meth)acrylate polymer, they function as flexibilizers and can enhance flexibility of the composition. Examples of the synthetic rubbers include EPT (ethylene/propylene/terpolymer). Examples of the thermoplastic elastomers include styrene-based elastomers, vinyl chloride-based elastomers, olefin-based elastomers, polyester-based elastomers, polyamide-based elastomers, urethane-based elastomers, an ethylene/vinyl acetate copolymer and a silicon polymer.

The molecular weight of the above elastomer is usually in the range of 1,000 to 1,000,000, preferably 2,000 to 500,000. The glass transition point (Tg) of the elastomer is usually not higher than 20° C., preferably not higher than 0° C.

In the (meth)acrylate polymers, organic or inorganic composites in which metal oxides or metal salts are coated with above-mentioned uncrosslinked polymers or crosslinked polymers are further included.

The weight-average molecular weight of the polymer, typically, the (meth)acrylate polymer, is preferably in the range of 1,000 to 1,000,000, more preferably 50,000 to 500,000, still more preferably 100,000 to 500,000. The above molecular weight is a molecular weight in terms of standard polymethyl methacrylate, as determined by gel permeation chromatography (GPC).

The polymer (B) may be composed of polymer particles. When the polymer (B) is composed of polymer particles, they may be polymer particles of plural kinds.

Examples of such polymer particles include polymer particles (b1) having a weight-average molecular weight of $30 \times 10^4$ to $60 \times 10^4$ and a specific surface area of 1.5 to 4.5 ($m^2/g$), polymer particles (b2) having a weight-average molecular weight of $5 \times 10^4$ to $20 \times 10^4$ and a specific surface area of 0.51 to 1.2 ($m^2/g$), and polymer particles (b3) having a weight-average molecular weight of $5 \times 10^4$ to $20 \times 10^4$ and a specific surface area of 0.1 to 0.5 ($m^2/g$).

The specific surface area of the polymer particles (b1) is preferably in the range of 1.5 to 4.5 ($m^2/g$), more preferably 2.0 to 4.0 ($m^2/g$).

The specific surface area of the polymer particles (b2) is preferably in the range of 0.51 to 1.2 ($m^2/g$), more preferably 0.6 to 1.0 ($m^2/g$).

The specific surface area of the polymer particles (b3) is preferably in the range of 0.1 to 0.5 ($m^2/g$), more preferably 0.2 to 0.45 ($m^2/g$).

The volume mean particle diameter of the polymer particles (b1) is usually in the range of 1 to 50 (μm), preferably 5 to 40 (μm). The volume mean particle diameter of the polymer particles (b2) is usually in the range of 0.1 to 40 (μm), preferably 1 to 20 (μm). The volume mean particle diameter of the polymer particles (b3) is usually in the range of 1 to 50 (μm), preferably 5 to 40 (μm).

When the polymer (B) is a polymer mixture composed of the polymer particles (b2) and the polymer particles (b3), and if necessary, the polymer particles (b1), the total amount of the polymer particles (b2) and the polymer particles (b3) is preferably not less than 2% by weight, more preferably not less than 5% by weight, based on the total weight of the polymer particles (b1), the polymer particles (b2) and the polymer particles (b3). The polymer mixture is sometimes composed of the polymer particles (b2) and the polymer particles (b3) in the total amount of 100% by weight.

When the total amount of the polymer particles (b2) and the polymer particles (b3) is not less than the lower limit of the above range, the polymer (B) is apt to be homogeneously dispersed in the monomer (A) and is more excellent in solubility in the monomer (A). Moreover, application of the composition to a wound or a soft tissue is made easier, and spreading of the composition over the surface of a wound or a soft tissue after the application tends to become smaller.

When the polymer particles (b1) are contained in the polymer particles, the total amount of the polymer particles (b2) and the polymer particles (b3) is preferably not more than 99% by weight, more preferably not more than 95% by weight, still more preferably not more than 90% by weight, based on the total weight of the polymer particles (b1), the polymer particles (b2) and the polymer particles (b3).

When the polymer particles (b1) are contained in the polymer particles, the content of the polymer particles (b1) is preferably not more than 98% by weight, more preferably not more than 95% by weight, based on the total weight of the polymer particles (b1), the polymer particles (b2) and the polymer particles (b3). The content of the polymer particles (b1) is preferably not less than 1% by weight, more preferably not less than 5% by weight, still more preferably not less than 10% by weight, based on the total weight of the polymer particles (b1), the polymer particles (b2) and the polymer particles (b3).

The amount of the polymer (B) is preferably in the range of 1 to 70 parts by weight, more preferably 10 to 65 parts by weight, still more preferably 13 to 65 parts by weight, much more preferably 13 to 60 parts by weight, based on 100 parts by weight of the total amount of the monomer (A), the polymer (B) and the polymerization initiator composition (C).

If the amount of the polymer (B) is less than the lower limit of the above range, progress of polymerization becomes difficult, adhesion effect is poor, and besides, there is a possibility that the mixture runs out of the desired area to obstruct the treatment. If the amount of the polymer (B) exceeds the upper limit of the above range, mixing with the monomer (A) becomes difficult. Further, because of rapid increase of viscosity, extrusion of the mixture from the container tends to become difficult. Furthermore, polymerization proceeds to immediately form a polymerization cured product in some cases, so that the composition tends to be not excellent in operability as an adhesive or a wound dressing.

When the polymer (B) is a (meth)acrylate polymer, the amount of the (meth)acrylate polymer is sometimes in the range of preferably 1 to 75 parts by weight, more preferably 1 to 73 parts by weight, still more preferably 10 to 73 parts by weight, much more preferably 15 to 73 parts by weight, particularly preferably 13 to 68 parts by weight, most preferably 21 to 64 parts by weight, based on 100 parts by weight of the total amount of the monomer (A), the (meth)acrylate polymer and the later-described polymerization initiator composition (C).

If the amount of the (meth)acrylate polymer is less than the lower limit of the above range, adhesive strength and other properties, such as flexural elastic modulus, tensile strength, compression strength and flexural strength, tend to become poor. If the amount of the (meth)acrylate polymer exceeds the upper limit of the above range, the viscosity is increased, and operations, such as application and injection, tend to become difficult.

When the polymer (B) is a (meth)acrylate polymer and is a mixture of the polymer particles (b1), (b2) and (b3), the following embodiments are preferable under the conditions that the total amount of the polymer particles (b1), (b2) and (b3) is 100% by weight and the total amount of the polymer particles (b2) and (b3) is not less than 2% by weight, preferably not less than 5% by weight.

When the amount of the polymer (B) is not less than 13 parts by weight but less than 28 parts by weight based on 100 parts by weight of the total amount of the monomer (A), the polymer (B) and the polymerization initiator composition (C), the amount of the polymer particles (b1) is preferably in the range of 10% by weight to 95% by weight, more preferably 15% by weight to 95% by weight, still more preferably 38% by weight to 95% by weight, the amount of the polymer particles (b2) is preferably not more than 90% by weight, more preferably not more than 85% by weight, still more preferably not more than 62% by weight, and the amount of the polymer particles (b3) is preferably not more than 90% by weight, more preferably not more than 85% by weight, still more preferably not more than 62% by weight;

when the amount of the polymer (B) is not less than 28 parts by weight but less than 68 parts by weight based on 100 parts by weight of the total amount of the monomer (A), the polymer (B) and the polymerization initiator composition (C), the amount of the polymer particles (b1) is preferably in the range of 10% by weight to 95% by weight, more preferably 10% by weight to 80% by weight, still more preferably 10% by weight to 60% by weight, the amount of the polymer particles (b2) is preferably not more than 90% by weight, and the amount of the polymer particles (b3) is preferably not more than 80% by weight, more preferably not more than 75% by weight; and when the amount of the polymer (B) is not less than 33 parts by weight but less than 68 parts by weight based on 100 parts by weight of the total amount of the monomer (A), the polymer (B) and the polymerization initiator composition (C), the amount of the polymer particles (b1) is preferably less than 10% by weight, more preferably not more than 8% by weight, still more preferably not more than 5% by weight, the amount of the polymer particles (b2) is preferably not more than 100% by weight, more preferably 20% by weight to 100% by weight, and the amount of the polymer particles (b3) is preferably not more than 100% by weight, more preferably not more than 80% by weight.

The adhesive composition for soft tissues, the adhesive composition for wound dressing or the wound dressing composition of the present invention is characterized by using the later-described organoboron compound (c1) as the initiator composition (C) contained, and when the organoboron compound is added to a composition containing a monomer, polymerization reaction begins slowly in a relatively early stage and proceeds. This greatly differs from a case of using a peroxide as a polymerization initiator where a relatively long time is required for the beginning of polymerization even if the polymerization initiator is added, and if the polymerization reaction once begins, the reaction proceeds rapidly and is completed in a relatively short time. In order to prepare a composition that is preferably used for wounds, soft tissues, etc., therefore, it is important to use such a polymer (B) of the present invention in such an amount as described above based on the monomer (A). By the use of such a polymer (B), not only can workability be ensured over a long time but also fluidity and application properties that are preferable in use for wounds, soft tissues, etc. can be ensured.

The polymerization initiator composition (C) contained in the adhesive composition for soft tissues, the adhesive composition for wound dressing or the wound dressing composition of the present invention contains an organoboron compound (c1) as an essential component, and can contain an aprotic solvent (c2) and an alcohol (c3), when needed. Since the polymerization initiator composition (C) containing the organoboron compound (c1) is contained in the composition of the present invention, a residue of the monomer (A) tends to be smaller when the whole composition is cured after application of the composition to a wound, a soft tissue or the like, as compared with a composition using a peroxide as a polymerization initiator. Further, a part of it penetrates into the epithelium and begins to undergo polymerization. Hence, the composition of the present invention is favorably used for organisms.

Examples of the organoboron compounds (c1) include trialkylboron, alkoxyalkylboron, dialkylborane and partially oxidized trialkylboron.

Examples of the trialkylborons include trialkylborons having an alkyl group of 2 to 8 carbon atoms, such as triethylboron, tripropylboron, triisopropylboron, tributylboron, tri-sec-butylboron, triisobutylboron, tripentylboron, trihexylboron, triheptylboron, trioctylboron, tricyclopentylboron and tricyclohexylboron. The alkyl group may be any of a straight-chain alkyl group, a branched alkyl group and a cycloalkyl group, and three alkyl groups contained in the trialkylboron may be the same or different.

The alkoxyalkylboron is, for example, monoalkoxydialkylboron or dialkoxymonoalkylboron. Specifically, the alkoxyalkylboron is, for example, monoalkoxydialkylboron such as butoxybutylboron. The alkyl group of the alkoxyalkylboron may be the same as or different from the alkyl part of the alkoxy group.

Examples of the dialkylboranes include dicyclohexylborane and diisoamylborane. Two alkyl groups of the dialkylborane may be the same or different. Two alkyl groups contained in the dialkylborane may be bonded to form a monocyclic structure or a bicyclo structure. Examples of such compounds include 9-borabicyclo[3.3.1]nonane.

The partially oxidized trialkylboron is a partially oxidized product of the above trialkylboron. As the partially oxidized trialkylboron, partially oxidized tributylboron is preferable. As the partially oxidized trialkylboron, partially oxidized trialkylboron obtained by the addition of oxygen in an amount of preferably 0.3 to 0.9 mol, more preferably 0.4 to 0.6 mol, based on 1 mol of the trialkylboron can be used.

Of the above organoboron compounds, tributylboron or partially oxidized tributylboron is preferable, and partially oxidized tributylboron is more preferable. When tributylboron or partially oxidized tributylboron is used as the organoboron compound (c1), not only is the operability of the composition improved but also the composition tends to have proper reactivity to organisms having moisture content. When tributylboron or partially oxidized tributylboron is used as the organoboron compound (c1), further, the reaction is initiated and proceeds even in a place of high moisture content such as an organism, so that the monomer rarely remains on the interface between the adhesive or the wound dressing and an organism. Hence, the injurious properties to the organism are extremely little. Such organoboron compounds (c1) can be used singly or in combination of two or more kinds.

In the polymerization initiator composition (C), an aprotic solvent (c2) may be contained. Since the aprotic solvent is contained in the polymerization initiator composition (C) as above and the organoboron compound is diluted, exothermic properties of the organoboron compound (c1) having ignition properties become gentler to suppress ignition properties, and hence, handling of the composition during transportation, storage and mixing is facilitated. In the case where an extremely large amount of an adhesive or a wound dressing is used, rapid generation of heat can be inhibited because of proper lowering of the exothermic properties, and consequently, damage of an organism that is in contact with the adhesive or the wound dressing of the present invention tends to be decreased. The boiling point of the aprotic solvent (c2) at 1 atm is usually in the range of 30° C. to 150° C., preferably 50° C. to 120° C. If the boiling point is lower than the lower limit of the above range, the aprotic solvent is evaporated or scattered from the polymerization initiator composition during transportation or storage, and the ignition property suppressing effect of the organoboron compound (c1) tends to be lowered. If the boiling point exceeds the upper limit of the above range, a residue of the aprotic solvent in a cured product formed from the adhesive composition or the wound dressing composition of the present invention is increased, and consequently, the adhesion performance of the composition tends to be lowered.

As the aprotic solvent (c2), a solvent that is unreactive to the organoboron compound (c1) and is capable of forming a homogeneous solution is preferable.

Examples of the aprotic solvents (c2) include:

hydrocarbons, such as pentane, hexane, cyclohexane, heptane, benzene and toluene;

halogenated hydrocarbons, such as fluorobenzene, 1,1-dichloroethane, 1,2-dichloroethane and so-called Freons®;

ethers, such as diethyl ether, diisopropyl ether, ethylene glycol dimethyl ether and tetrahydrofuran;

ketones, such as acetone, methyl ethyl ketone and diethyl ketone; and esters, such as methyl acetate, ethyl acetate and isopropyl acetate.

Of these, saturated aliphatic hydrocarbons, such as pentane, hexane and heptane, ethers and esters are preferable, and hexane, diisopropyl ether and ethyl acetate are more preferable.

These aprotic solvents (c2) can be used singly or in combination of two or more kinds.

The content of the aprotic solvent (c2) in the polymerization initiator composition (C) is preferably in the range of 30 to 80 parts by weight based on 100 parts by weight of the organoboron compound (c1).

If the content of the aprotic solvent (c2) is less than the lower limit of the above range, satisfactory dilution effect is not obtained, and the effect to suppress generation of heat or ignition tends to be insufficient. On the other hand, if the content of the aprotic solvent (c2) exceeds the upper limit of the above range, polymerization initiation ability of the polymerization initiator composition (C) tends to become lower than needed.

In the polymerization initiator composition (C), an alcohol (c3) may be further contained in addition to the aprotic solvent (c2). By adding a small amount of the alcohol (c3) to the polymerization initiator composition (C), the reaction by the organoboron compound (c1) is made still gentler without lowering the polymerization activity, and even if the composition is brought into contact with paper or the like in air, burning or ignition tends to be suppressed.

Examples of the alcohols (c3) include methanol, ethanol, n-propanol and its isomers, n-butanol and its isomers, n-pentanol and its isomers, n-hexanol and its isomers, and n-heptanol and its isomers.

Of these alcohols (c3), alcohols of 4 or less carbon atoms, namely, methanol, ethanol, n-propanol and its isomers, and n-butanol and its isomers are preferable, and ethanol and n-propanol are more preferable.

These alcohols (c3) can be used singly or in combination of two or more kinds.

The content of the alcohol (c3) in the polymerization initiator composition (C) is preferably in the range of 0.2 to 5 parts by weight, more preferably 0.3 to 4.5 parts by weight, still more preferably 0.5 to 4 parts by weight, based on 100 parts by weight of the organoboron compound (c1).

If the content of the alcohol (c3) is less than the lower limit of the above range, satisfactory dilution effect is not obtained, and the effect to suppress generation of heat or ignition tends to be insufficient. On the other hand, if the content of the alcohol (c3) exceeds the upper limit of the above range, polymerization initiation ability of the polymerization initiator composition (C) tends to become lower than needed.

When the alcohol (c3) and the aprotic solvent (c2) are used in combination, the content of the aprotic solvent (c2) in the polymerization initiator composition (C) is preferably in the range of 5 to 40 parts by weight, more preferably 10 to 30 parts by weight, still more preferably 10 to 25 parts by weight, based on 100 parts by weight of the organoboron compound (c1).

If the content of the aprotic solvent (c2) is less than the lower limit of the above range based on 100 parts by weight of the organoboron compound (c1), the effect to suppress generation of heat or ignition tends to be insufficient. On the other hand, if the content of the aprotic solvent (c2) exceeds the upper limit of the above range based on 100 parts by weight of the organoboron compound (c1), polymerization initiation ability of the polymerization initiator composition (C) tends to be lowered.

The amount of the polymerization initiator composition (C) is preferably in the range of 0.05 to 20 parts by weight, more preferably 0.5 to 10 parts by weight, still more preferably 1 to 3 parts by weight, based on 100 parts by weight of the total amount of the monomer (A), the polymer (B) and the polymerization initiator composition (C).

If the amount of the polymerization initiator composition (C) is less than the lower limit of the above range, progress of polymerization is difficult, and the adhesion effect tends to become poor. If the amount of the polymerization initiator composition (C) exceeds the upper limit of the above range, there is a possibility of lowering viscosity because of dilution or a possibility of exerting evil influence on safety. Moreover, it is presumed that rapid polymerization proceeds to form a polymerization product immediately, and therefore, the composition tends to be not excellent in operability as an adhesive or a wound dressing.

In the adhesive composition or the wound dressing composition, other components may be further contained when needed, as long as they do not exert evil influence on the performance of the composition.

As one of the other components, a polymerization inhibitor (D) can be mentioned. Examples of the polymerization inhibitors (D) include hydroquinone compounds, such as hydroquinone and dibutylhydroquinone, hydroquinone monomethyl ether, phenols, such as 2,6-di-tert-butylphenol and 2,6-di-tert-butyl-p-cresol, catechol, pyrogallol, benzoquinone, 2-hydroxybenzoquinone, p-methoxyphenol, t-butylcatechol, butylated hydroxyanisole, butylated hydroxytoluene and t-butylhydroquinone. Of these, a mixture of hydroquinone monomethyl ether and 2,6-di-tert-butyl-p-cresol is preferably used.

Of these polymerization inhibitors (D), hydroquinone monomethyl ether is sometimes preferable from the viewpoint of good stability of the hydroquinone monomethyl ether itself.

The above polymerization inhibitors (D) can be used singly or in combination of two or more kinds.

When the polymerization inhibitor (D) is added, the amount thereof is preferably in the range of 10 to 5000 ppm, more preferably 50 to 1000 ppm, still more preferably 50 to 500 ppm, based on the whole amount of the adhesive composition or the wound dressing composition.

It is also preferable to add the polymerization inhibitor (D) in an amount of 10 to 5000 ppm based on the monomer (A).

By preparing such a composition, for example, when an adhesive is applied to an adherend, such as the affected part (affected part that is not dried because of exudate from the incised part) in the surgical operation, a wound or a soft tissue, the composition becomes more excellent in ensuring application properties and a proper curing time and can be more stably handled as an adhesive or a dressing than before. Moreover, the composition is excellent in workability.

Although the amount of the polymerization inhibitor (D) is as described above, the polymerization inhibitor (D) is more preferably added in an amount of 50 to 1000 ppm, still more preferably 50 to 500 ppm, based on the monomer (A). By preparing such a composition, for example, the composition can be not only handled stably during application but also cured efficiently after application. If the content of the polymerization inhibitor (D) is less than the lower limit of the above range, curing takes place immediately after mixing of the monomer (A), the polymer (B) and the polymerization initiator composition (C), and hence, application tends to become difficult. On the other hand, if the content of the polymerization inhibitor (D) exceeds the upper limit of the above range, polymerization initiation ability of the polymerization initiator composition (C) is lowered, and the curing time becomes longer than needed. Hence, medical use of the composition tends to become difficult.

As one of the other components, an ultraviolet light absorber can be further mentioned. Examples of the ultraviolet light absorbers include:

benzotriazole compounds, such as 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, a mixture of 2-(3'-tert-butyl-2'-hydroxy-5'-(2-isooctyloxycarbonylethyl)phenyl)benzotriazole and 2,2'-methylene-bis[4-(1,1,3,3-tetramethylbutyl)-6-benzotriazol-2-ylphenol], an ester interchange reaction product of 2-[3'-tert-butyl-5'-(2-methoxycarbonylethyl)-2'-hydroxyphenyl]benzotriazole with polyethylene glycol 300, and [[R—CH$_2$CH$_2$—COOCH$_2$]$_3$]$_2$— (wherein R is 3'-tert-butyl-4'-hydroxy-5'-2H-benzotriazol-2-ylphenyl);

benzophenone compounds, such as 2,4-dihydroxybenzophenone, 2-hydroxy-4-methoxybenzophenone, 2-hydroxy-4-octoxybenzophenone, 2-hydroxy-4-decyloxybenzophenone, 2-hydroxy-4-dodecyloxybenzophenone, 2-hydroxy-4-benzyloxybenzophenone, 2,2',4,4'-tetrahydroxybenzophenone, and 2,2'-dihydroxy-4,4'-dimethoxybenzophenone;

4-tert-butylphenyl salicylate, phenyl salicylate, octylphenyl salicylate, dibenzoylresorcinol, bis(4-tert-butylbenzoyl)resorcinol, benzoylresorcinol, butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl benzoate, and 3,5-di-tert-butyl-4-hydroxybenzyl benzoate;

hindered amine compounds, such as bis(2,2,6,6-tetramethylpiperidyl)sebacate, bis(2,2,6,6-tetramethylpiperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, a condensation product of 1-hydroxyethyl-2,2,6,6-tetramethyl-4-hydroxypiperidine and succinic acid, a condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethyl-4-piperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, a condensation product of N,N'-bis(2,2,6,6-tetramethyl-4-piperidyl)hexamethylenediamine and 4-morpholino-2,6-dichloro-1,3,5-triazine, a condensation product of 2-chloro-4,6-di-(4-n-butylamino-2,2,6,6-tetramethylpiperidyl)-1,3,5-triazine and 1,2-bis(3-aminopropylamino)ethane, a condensation product of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, and 3-dodecyl-1-(1,2,2,6,6-pentamethyl-4-piperidyl)pyrrolidine-2,5-dione;

oxalamide compounds, such as 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, a mixture of 2-ethoxy-5-tert-butyl-2'-ethyloxanilide and 2-ethoxy-2'-ethyl-5,4'-di-tert-butyloxanilide, a mixture of o-methoxy- and p-methoxy-di-substituted oxanilides, and a mixture of o-ethoxy- and p-ethoxy-di-substituted oxanilides;

2-(2-hydroxyphenyl)-1,3,5-triazine compounds, such as 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-

1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine, and 2-[4-dodecyl/tridecyloxy-(2-hydroxypropyl)oxy-2-hydroxyphenyl]-4,6-bis(2,4-dimethylphenyl)-1,3,5-triazine; and phosphite compounds or phosphonite compounds, such as triphenyl phosphite, diphenylalkyl phosphite, phenyldialkyl phosphite, tris(nonylphenylphosphite), trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl)pentaerythritol diphosphite, bisisodecyloxypentaerythritol diphosphite, bis(2,4-di-tert-butyl-6-methylphenyl)pentaerythritol diphosphite, bis(2,4,6-tri-tert-butylphenyl)pentaerythritol diphosphite, tristearyl sorbityl triphosphite, tetrakis(2,4-di-tert-butylphenyl)-4,4'-biphenylene diphosphonite, 6-isooctyloxy-2,4,8,10-tetra-tert-butyl-12H-dibenzo[d.g]-1,3,2-dioxaphosphocine, 6-fluoro-2,4,8,10-tetra-tert-butyl-12-methyldibenzo[d,g]-1,3,2-dioxaphosphocine, bis(2,4-di-tert-butyl-6-methylphenyl)methyl phosphite, and bis(2,4-di-tert-butyl-6-methylphenyl)ethyl phosphite.

As the ultraviolet light absorber, a benzotriazole compound is preferable.

When the ultraviolet light absorber is added, the amount thereof is preferably in the range of 10 to 1,000 ppm, more preferably 100 to 800 ppm, based on the monomer (A). By adding the ultraviolet light absorber as above, coloring of a liquid containing a monomer is suppressed, and storage stability of the monomer itself tends to be enhanced.

As one of the other components, a plasticizer can be further mentioned.

Examples of the plasticizers include hydroxycarboxylic acid esters, such as citrate esters, isocitrate esters, tartrate esters, malate esters, lactate esters, glycerate esters and glycolate esters; trimethyl trimellitate ester, diethylene glycol dibenzoate ester, diethyl malonate ester, triethyl o-acetylcitrate ester esters, benzyl butyl phthalate ester, dipropylene glycol dibenzoate ester, diethyl adipate ester, tributyl o-acetylcitrate ester, dimethyl sebacate ester, and alkylene glycol diesters.

Although the amount of the plasticizer is properly selected according to the type of the material, the plasticizer is used so that it may be usually contained in an amount of 0 to 30% by weight, preferably 0 to 20% by weight, more preferably 0 to 10% by weight, in the whole adhesive composition or wound dressing composition.

As one of the other components, a preservative can be further mentioned.

Examples of the preservatives include:

methylparaben, methylparaben sodium, ethylparaben, propylparaben, propylbaraben sodium, butylparaben;

cresol, chlorocresol;

resorcinol, 4-n-hexylresorcinol, 3a,4,7,7a-tetrahydro-2-((trichloromethyl)thio)-1H-isoindole-1,3(2H)dione;

benzalkonium chloride, benzalkonium sodium chloride, benzethonium chloride;

benzoic acid, benzyl alcohol, cetylpyridinium chloride, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, phenylmercuric compounds, such as phenylmercuric borate, phenylmercuric nitrate and phenylmercuric acetate, and formaldehyde.

As examples of the other components, there can be further mentioned anti-infectious agents, antibiotics, antibacterial agents, anti-virus agents, analgesics, compositions of analgesics, anorectic drugs, antihelmintic drugs, antiarthritic agents, antiasthmatic drugs, anticonvulsants, antidepressants, antidiuretics, antidiarrheal agents, antihistamine drugs, anti-inflammatory drugs, antimigraine drugs, antiemetic agents, antineoplastic drugs, antiparkinsonian agents, antipruritic drugs, antipsychotics, antipyretic drugs, antispasmodic drugs, anticholinergic agents, sympathomimetic agents, cardiovascular drugs, antiarrhythmic drugs, antihypertensive drugs, diuretics, vasodilators, immunosuppressant drugs, muscle-relaxant drugs, parasympatholytic drugs, stimulants, sedative drugs, tranquilizers, cholinergic agents, chemotherapeutic drugs, radio pharmaceuticals, bone inductive drugs, heparin neutralizer agents of static bladder, procoagulants, hemostatic agents, xanthine derivatives, hormones, proteins of natural origin or proteins synthesized by genetic engineering, polysaccharides, glycoproteins, lipoproteins, oligonucleotides, antibody, antigen, vasopressin, vasopressin analogs, epinephrine, selectin, clot promoting toxicants, plasminogen activating factor inhibitors, platelet activators, and synthetic peptides having hemostatic action. Since these components are contained, the composition of the present invention can be used for the drug delivery system or the purpose of regenerative medicine.

Examples of the antibacterial agents include:

element iodine, solid polyvinylpyrrolidone iodine, polyvinylpyrrolidone iodine;

phenol compounds, such as tribromophenol, trichlorophenol, tetrachlorophenol, nitrophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol, 2,4-dichloro-3,5-dimethylphenol, 4-chlorothymol, chlorophene, triclosan, fenticlor, phenol, 2-methylphenol, 3-methylphenol, 4-methylphenol, 4-ethylphenol, 2,4-dimethylphenol, 2,5-dimethylphenol, 3,4-dimethylphenol, 2,6-dimethylphenol, 4-n-proylphenol, 4-n-butylphenol, 4-n-aminophenol, 4-tert-amylphenol, 4-n-hexylphenol, 4-n-heptylphenol, monoalkylhalophenol, polyalkylhalophenol, aromatic halophenol, and ammonium salts, alkali metal salts and alkaline earth metal salts of these substances;

silver nitrate, hexachlorophene, merbromin, tetracycline HCl, tetracycline hydrate and erythromycin.

In the adhesive composition or the wound dressing composition, angiogenic factor, basic fibroblast growth factor, epidermal growth factor, etc. may be contained as the above proteins for the purpose of accelerating tissue reparation.

As examples of the other components, there can be further mentioned perfumes, such as orange oil, grapefruit oil, lemon oil, lime oil, clove oil, wintergreen oil, peppermint oil, peppermint spirit, banana distillate, cucumber distillate, honey distillate, rose water, menthol, anethole, alkyl salicylate, benzaldehyde, monosodium glutamate, ethylvanillin, thymol and vanillin.

Furthermore, an inorganic filler, an organic filler, an organic composite filler, a filler colorant, etc. may be contained as the other components.

Examples of the inorganic fillers include: metal oxide powders, such as zirconium oxide, bismuth oxide, titanium oxide, zinc oxide and aluminum oxide particles;

metal salt powders, such as bismuth carbonate, zirconium phosphate and barium sulfate;

glass fillers, such as silica glass, aluminum-containing glass, barium-containing glass, strontium-containing glass and zirconium silicate glass;

fillers having silver sustained-release property; and fillers having fluorine sustained-release property.

From the viewpoint of formation of strong bonding between an inorganic filler and the monomer (A) after curing, it is preferable to use an inorganic filler having been subjected to surface treatment such as silane treatment or polymer coating.

These inorganic fillers can be used singly or in combination of two or more kinds.

As examples of the other components, X-ray contrast media, such as barium sulfate and zirconium oxide, can be further mentioned. In the present invention, zirconium oxide is preferable as the X-ray contrast medium.

The adhesive composition for soft tissues, the adhesive composition for wound dressing or the wound dressing composition of the present invention is characterized by having a viscosity of 0.4 to 75,000 cp within 30 seconds after mixing of the components (A), (B) and (C) and the components to be contained when needed.

Since the viscosity is in the above range, the composition is easily applied as an adhesive or a wound dressing.

From the viewpoints of operability and fluidity, the viscosity is preferably in the range of 0.4 to 10,000 cp, more preferably 1 to 10,000 cp.

The adhesive composition or the wound dressing composition of the present invention preferably has a viscosity of to 1,000,000 cp, more preferably 20 to 1,000,000 cp, still more preferably 30 to 800,000 cp, 60 seconds after mixing of the components (A), (B) and (C) and the components to be contained when needed.

Since the viscosity is in the above range, the composition can be easily extruded from a container as an adhesive or a wound dressing, and has excellent operability such as ease of application.

The composition of the present invention is excellent in operability as an adhesive or a wound dressing, namely, application properties such as fluidity. Even if the composition of the present invention is compared with a composition using a peroxide as an initiator component, the operator tends to be able to ensure a longer time than the time necessary for the mixing operation, and also from this viewpoint, the composition of the present invention is excellent in operability.

A film, which is obtained from the adhesive composition or the wound dressing composition of the present invention, is given 24 hours after the preparation of the composition and has a thickness of not less than 1 μm (preferably not more than 1 cm), a length of not less than 25 mm and a width of not less than 2 mm, preferably has a flexural elastic modulus, as measured under the conditions of a test rate of 2 mm/min, of not more than 750 MPa, more preferably not more than 740 MPa, still more preferably not more than 730 MPa. A film, which is obtained from the composition, is given 24 hours after the preparation of the composition and has a thickness of not less than 1 μm (preferably not more than 1 cm), a length of not less than 25 mm and a width of not less than 2 mm, may preferably have a flexural elastic modulus, as measured under the conditions of a test rate of 2 mm/min, of not more than 750 MPa, more preferably not more than 600 MPa, still more preferably not more than 550 MPa.

The flexural elastic modulus of the above cured product may be preferably not less than 100 MPa, more preferably not less than 150 MPa, still more preferably not less than 200 MPa.

A film, which is obtained from the adhesive composition or the wound dressing composition of the present invention, is given 24 hours after the preparation of the composition and has a thickness of not less than 1 μm (preferably not more than 1 cm), a length of not less than 25 mm and a width of not less than 2 mm, preferably has a tensile elongation, as measured under the conditions of a test rate of 1 mm/min, of not less than 5%, more preferably not less than 15%, still more preferably not less than 25%.

The tensile elongation may be preferably not less than 5%, more preferably not less than 7%, still more preferably not less than 9%. The tensile elongation may be preferably not less than 30%, more preferably not less than 40%, still more preferably not less than 50%.

A cured product obtained from the adhesive composition or the wound dressing composition of the present invention provides a coating film having properties excellent for soft tissues or the skin, and is excellent in adhesion to the skin on the bending portions, namely, portions where flexing or bending of a joint or the like is made.

In the present invention, the monomer (A), the polymer (B), the polymerization initiator composition (C) and the components to be contained when needed are previously mixed to prepare an adhesive composition or a wound dressing composition, and the composition can be used by applying it to a wound (affected part in the surgical operation, wound to be dressed), a soft tissue or the like.

When these components are mixed, the order of mixing is not specifically restricted, but it is preferable that the monomer (A) is first mixed with the polymerization initiator composition (C) and subsequently mixed with the polymer (B), from the viewpoint that the components can be homogeneously and stably mixed.

When the adhesive composition or the wound dressing composition contains the polymerization inhibitor (D), it is preferable that a mixture of the monomer (A) and the polymerization inhibitor (D) is first mixed with the polymerization initiator composition (C) and subsequently mixed with the polymer (B).

Prior to or during curing of the adhesive composition or the wound dressing composition of the present invention, the composition may be irradiated with electromagnetic waves, such as visible light, ionizing radiation (e.g., γ-rays) or electron rays, to perform sterilization. Irradiation with visible light is sometimes desirable because the visible light does not greatly change the curing conditions. Sterilization may be carried out by treatment with gas, such as dry heat, steam, ethylene oxide (EO) or hydrogen peroxide, filtration, treatment with liquid, autoclave sterilization, or the like.

Prior to application of the adhesive composition or the wound dressing composition of the present invention to a wound, a soft tissue or the like, the surface of the wound, the soft tissue or the like may be disinfected with a disinfectant such as alcohol.

Prior to application of the adhesive composition or the wound dressing composition of the present invention to a wound, a soft tissue or the like, pretreatment may be further carried out for the purpose of improving adhesion properties. The pretreatment liquid is, for example, an aqueous solution containing 1 to 15% by weight of citric acid and 1 to 5% by weight of iron(III) chloride.

When the adhesive composition or the wound dressing composition of the present invention is applied to a wound, the composition is polymerized and cured to form a film, and therefore, the composition can be used for bonding the wound or covering the surface of the wounded area (that is, after the wound edges are put together, the adhesive is applied to the surface of the wounded area, and it adheres to the surface and is cured). For the purpose of fixing or protecting the edge or the whole of the cured film or maintaining or increasing the adhesive force, covering articles, such as film, sheet, paper, plaster, bondage and gauze, may be used during or after application of the composition to a wound, a soft tissue surface or the like. These covering articles may have adhesiveness, or may have tackiness.

The adhesive composition or the wound dressing composition can be applied to a wound during or after application of an alginate dressing material, a hydrogel or a hydropolymer to the wound.

If there is a fear that the form or the performance of the adhesive composition or the wound dressing composition of the present invention varies because of preservation or storage of a long time, thereby impairing the effect of the present invention, it is possible that the components comprising the monomer (A), the polymer (B), the polymerization initiator composition (C) and the components to be contained when needed, such as the polymerization inhibitor (D), are stored in the form of a kit which is used as an adhesive for soft tissues, an adhesive for wound dressing or a wound dressing and has two or more members in which the above components are encased independently or in groups divided in an optional combination, and prior to use, the components are mixed to form the adhesive composition or the wound dressing composition. The members for encasing the components therein are, for example, sealable resin containers having gas barrier properties in order to prevent evaporation or scattering of the monomer (A) and the polymerization initiator composition (C), or glass syringes. The members for encasing the polymer (B) therein are, for example, resin containers having good sealing properties or glass containers in order to prevent moisture absorption. As for the quantity to be encased, there is a case where the quantity that is used up one time is encased or a case where the quantity that is used plural times is encased.

Examples of manners to store the components include a manner in which the components are divided into three groups consisting of a mixture of the component (A) and the components to be contained when needed, a mixture of the component (B) and the components to be contained when needed, and a mixture of the component (C) and the components to be contained when needed, followed by storing them; a manner in which the components are divided into two groups consisting of a mixture of the component (A), the component (B) and the components to be contained when needed, and the component (C), followed by storing them; a manner in which the components are divided into two groups consisting of a mixture of the component (A) and the component (B), and a mixture of the component (C) and the components to be contained when needed, followed by storing them; a manner in which the components are divided into two groups consisting of a mixture of the component (A), the component (B) and a part of the components to be contained when needed, and a mixture of the component (C) and a residue of the components to be contained when needed, followed by storing them; a manner in which the components are divided into two groups consisting of a mixture of the component (A) and the components to be contained when needed, and a mixture of the component (B) and the component (C), followed by storing them; a manner in which the components are divided into two groups consisting of the component (A), and a mixture of the component (B), the component (C) and the components to be contained when needed, followed by storing them; and a manner in which the components are divided into two groups consisting of a mixture of the component (A) and a part of the components to be contained when needed, and a mixture of the component (B), the component (C) and a residue of the components to be contained when needed, followed by storing them.

When the polymerization inhibitor (D) is contained, examples of manners to store the components include a manner in which the components are divided into three groups consisting of a mixture of the component (A) and the components to be contained when needed, a mixture of the component (B) and the components to be contained when needed, and a mixture of the component (C) and the components to be contained when needed, followed by storing them; a manner in which the components are divided into two groups consisting of a mixture of the component (A), the component (B), the component (D) and the components to be contained when needed, and the component (C), followed by storing them; a manner in which the components are divided into two groups consisting of a mixture of the component (A), the component (B) and the component (D), and a mixture of the component (C) and the components to be contained when needed, followed by storing them; a manner in which the components are divided into two groups consisting of a mixture of the component (A), the component (B), the component (D) and a part of the components to be contained when needed, and a mixture of the component (C) and a residue of the components to be contained when needed, followed by storing them; a manner in which the components are divided into two groups consisting of a mixture of the component (A), the component (D) and the components to be contained when needed, and a mixture of the component (B) and the component (C), followed by storing them; a manner in which the components are divided into two groups consisting of a mixture of the component (A) and the component (D), and a mixture of the component (B), the component (C) and the components to be contained when needed, followed by storing them; and a manner in which the components are divided into two groups consisting of a mixture of the component (A), the component (D) and a part of the components to be contained when needed, and a mixture of the component (B), the component (C) and a residue of the components to be contained when needed, followed by storing them.

When a mixture of a monomer having an acidic group and a monomer having no acidic group is used as the monomer (A), the components may be stored in such a manner that the monomer having an acidic group is not in contact with the polymerization initiator composition, in addition to the above manners. Examples of such manners include a manner in which the components are divided into two groups consisting of a mixture of the monomer having an acidic group, the component (B) and the components to be contained when needed, and a mixture of the monomer having no acidic group and the component (C), followed by storing them; a manner in which the components are divided into two groups consisting of a mixture of the monomer having an acidic group and the component (B), and a mixture of the monomer having no acidic group, the component (C) and the components to be contained when needed, followed by storing them; a manner in which the components are divided into two groups consisting of a mixture of the monomer having an acidic group and the components to be contained when needed, and a mixture of the monomer having no acidic group, the component (B) and the component (C), followed by storing them; and a manner in which the components are divided into two groups consisting of the monomer having an acidic group, and a mixture of the monomer having no acidic group, the component (B), the component (C) and the components to be contained when needed, followed by storing them.

The components divided into two groups are placed in separate members, e.g., containers such as syringes, and the members are encased in a kit that is used as an adhesive for soft tissues, an adhesive for wound dressing or a wound dressing, and the kit can be provided as an article.

The constitution of the kit is not specifically restricted as long as there is no fear that the form or the performance is changed by the storage to impair the effect of the present invention, but the kit preferably has constitution in which the monomer (A), the polymer (B) and the polymerization initiator composition (C) are each independently encased, and the monomer (A) is first mixed with the polymerization initiator composition (C) containing an organoboron compound and subsequently mixed with the polymer (B). By virtue of such constitution, an adhesive composition or a wound dressing composition having more stable performance tends to be obtained.

Examples of such kits include:

a kit having members (e.g., containers, syringes) in which the monomer (A), the polymer (B) and the polymerization initiator composition (C) are each independently encased and having a member (e.g., mixing container, mixing dish) for taking out the encased components from the members and mixing them; and a kit having one container which has three or more chambers separated by partitions, in said chambers the monomer (A), the polymer (B) and the polymerization initiator composition (C) being each independently encased, and having a stirring unit for mixing the monomer (A) and the polymerization initiator composition (C) with the polymer (B), said components (A) and (C) having passed through a bypass formed in a syringe owing to rupture of the partitions or shifting of the partitions.

When the kit contains the polymerization inhibitor (D), the kit preferably has constitution in which a mixture containing the monomer (A) and the polymerization inhibitor (D), the polymer (B) and the polymerization initiator composition (C) are each independently encased, and the mixture containing the monomer (A) and the polymerization inhibitor (D) is first mixed with the polymerization initiator composition (C) containing an organoboron compound and subsequently mixed with the polymer (B). By virtue of such constitution, an adhesive for soft tissues, an adhesive for wound dressing or a wound dressing having more stable performance tends to be obtained.

Examples of such kits include:

a kit having members (e.g., containers, syringes) in which a mixture containing the monomer (A) and the polymerization inhibitor (D), the polymer (B) and the polymerization initiator composition (C) are each independently encased and having a member (e.g., mixing container, mixing dish) for taking out the encased components from the members and mixing them; and a kit having one container which has three or more chambers separated by partitions, in said chambers a mixture containing the monomer (A) and the polymerization inhibitor (D), the polymer (B) and the polymerization initiator composition (C) being each independently encased, and having a stirring unit for mixing the mixture containing the monomer (A) and the polymerization inhibitor (D) and the polymerization initiator composition (C) with the polymer (B), said mixture and said component (C) having passed through a bypass formed in a syringe owing to rupture of the partitions or shifting of the partitions.

The kit having one container wherein the components are encased in the separated three or more chambers requires less labor as compared with a means wherein the composition of the present invention is divided, placed in two or more members, typically containers, and mixed immediately before use. Moreover, this kit uses no mixing container or the like and can be economically used by taking a necessary amount of the composition out of the container and bringing it into contact with a jig such as sponge.

It is also possible that a jig that is used for applying the adhesive composition or the wound dressing composition to a wound, a soft tissue or the like is allowed to contain a part or the whole of the polymerization initiator composition (C) in advance, and the jig is brought into contact with the monomer (A) or a mixture containing the monomer (A) and the polymerization inhibitor (D), the polymer (B) and the components to be contained when needed to prepare the adhesive composition or the wound dressing composition of the present invention in situ, followed by applying it to a wound, a soft tissue or the like.

Examples of the jigs for applying the composition to a wound, a soft tissue or the like include a brush, a fiber ball, a cloth, a sponge ball and a piece of sponge.

In the kit, the aforesaid disinfectant liquid such as alcohol, the aforesaid pretreatment liquid for improving adhesion properties, the aforesaid covering article, etc. may be included.

When the components of the composition are stored in the kit, they may be subjected to sterilization treatment with electromagnetic waves such as visible light preferably under the conditions that the components are not modified (e.g., monomer is not cured).

The adhesive composition for soft tissues, the adhesive composition for wound dressing or the wound dressing composition of the present invention can be used for, for example, adhesion of organism tissues, such as closure, protection or obstruction of wounds, fixing (adhesion) of soft tissue graft, hemostasis, vascular anastomosis, vascular obstruction, bronchial anastomosis, bronchial obstruction and ophthalmologic operations.

By directly applying the composition of the present invention to a wound formed in the outer skin of an organism such as skin or mucous membrane, the opening of the wound can be easily closed. Moreover, the composition of the present invention can be used also for fixing a graft to the skin transplantation area in the skin transplantation.

When the composition of the present invention is used as a wound dressing, the adhesive is not applied to the wound surface usually, but the adhesive is applied to the surface of the wounded area after the wound edges are put together, and it adheres to the surface and is cured. In the case of a wound having no incised surface, such as scratch, crush wound or contused wound, the composition may be directly applied to the affected part in order to dress the wound.

EXAMPLES

The present invention is further described with reference to the following examples, but it should be construed that the present invention is in no way limited to those examples.

Examples 1A to 18A

Reagents

In the examples, the following compounds and composition were used as the monomer (A), the polymer (B) and the polymerization initiator composition (C).

Monomer (A): 4-META/MMA, methyl methacrylate solution of 4-methacryloxyethyltrimellitic anhydride (weight ratio: about 5%)

Polymer (B): mixture of three kinds of the following PMMA (polymethyl methacrylates) (b1) to (b3) and pigment The weight ratios of these components are as follows: in 100 parts by weight of the total amount of the three kinds of PMMA and the pigment, (b1) is contained in an amount of 20.03 parts by weight, (b2) is contained in an amount of 62.5 parts by weight, (b3) is contained in an amount of 12.5 parts by weight, and the pigment is contained in the residual amount.

Molecular weights and properties of the PMMA (b1) to (b3) are as follows.

(b1) weight-average molecular weight: 450,000, volume mean particle diameter: 26.7 μm, specific surface area: 2.913 m$^2$/g (b2) weight-average molecular weight: 140,000, volume mean particle diameter: 8.2 μm, specific surface area: 0.827 m$^2$/g (b3) weight-average molecular weight: 140,000, volume mean particle diameter: 24.6 μm, specific surface area: 0.371 m$^2$/g The volume mean particle diameter of PMMA (refractive index: 1.49) was measured in the following manner. As a dispersion medium, special grade reagent methanol (refractive index: 1.33, available from Wako Pure Chemical Industries, Ltd.) was used. The PMMA was dispersed in the dispersion medium by an ultrasonic homogenizer integrated in the apparatus for 5 minutes (output: 25 W), and the measurement was carried out under the concentration conditions of the proper range of the apparatus Loading Index at a circulation rate of 50% (100%:65 ml/sec) by the use of Microtrac MT3300EXII (particle size distribution meter manufactured by Microtrac Inc.).

The specific surface area is a value determined by nitrogen gas adsorption at the liquid nitrogen temperature (77 K) using Autosorb 3 (manufactured by Quantachrome Instruments), and is a value measured by BET method.

Polymerization initiator composition (C): TBB A type, namely, partially oxidized tributylboron: 80 parts by weight, hexane: 19 parts by weight, ethanol: 1 part by weight Evaluation of Viscosity In a sample tube, the polymer (B) was weighed in accordance with a blending ratio described in Examples 1A to 9A of the following Table 1. In the sample tube in which the polymer (B) had been weighed, the monomer (A) and the polymerization initiator composition (C), which had been mixed together in a different sample tube in accordance with a blending ratio described in Examples 1A to 9A of the following Table 1 similarly to the above, were injected, and they were mixed together at 25° C. to prepare an adhesive composition or a wound dressing composition of the present invention. 30 seconds after the preparation, viscosity of the composition was measured. The viscosity at the time of preparation was not less than 0.4 cp, and it was confirmed that the viscosity increased with time. The viscosity was measured by an E type viscometer (manufactured by Tokyo Keiki Inc., EHP type) at 25° C. The evaluation results are set forth in Table 1.

Evaluation of Application Properties

In a syringe having a cap at the luer part, the polymer (B) was weighed in accordance with a blending ratio described in Examples 1A to 9A of the following Table 1. In this syringe, the monomer (A) and the polymerization initiator composition (C), which had been mixed together in a sample tube in accordance with a blending ratio described in Examples 1A to 9A of the following Table 1 similarly to the above, were injected, and they were mixed together at 25° C. Thereafter, the cap of the syringe was removed, then a nozzle having a width of 1 cm and a thickness of 1 mm was fitted, and 1 ml of the composition mixed was applied by 4 cm onto a polyethylene sheet. The application properties were evaluated based on the 5-grade evaluation of 1 to 5. That is to say, a case where the width of the applied composition was not less than 1 cm but less than 1.2 cm was evaluated to be 5; a case where the width of the applied composition was not less than 1.2 cm but less than 1.4 cm was evaluated to be 4; a case where the width of the applied composition was not less than 1.4 cm but less than 1.6 cm was evaluated to be 3; a case where the width of the applied composition was not less than 1.6 cm was evaluated to be 2; and a case where application was impossible was evaluated to be 1. The evaluation results are set forth in Table 1.

It was confirmed that in the case of the adhesive composition or the wound dressing composition containing the components (A), (B) and (C) and having a viscosity of less than 0.4 cp after 30 seconds, the width of the applied composition was too large, and in the case of the composition having a viscosity of more than 75000 cp after 30 seconds, application using a syringe was impossible.

TABLE 1

| | Adhesive composition or wound dressing composition (part(s) by weight) | Viscosity 30 seconds after mixing (cp) | Application properties |
|---|---|---|---|
| Ex. 1A | Monomer (A): 1680 mg (87.2) Polymer (B): 192.7 mg (10.0) Polymerization initiator composition (C): 54 mg (2.8) | 0.5 | 2 |
| Ex. 2A | Monomer (A): 1680 mg (82.4) Polymer (B): 305 mg (15.0) Polymerization initiator composition (C): 54 mg (2.6) | 1 | 4 |
| Ex. 3A | Monomer (A): 1680 mg (77.5) Polymer (B): 433.5 mg (20.0) Polymerization initiator composition (C): 54 mg (2.5) | 24 | 4 |
| Ex. 4A | Monomer (A): 1680 mg (72.7) Polymer (B): 578 mg (25.0) Polymerization initiator composition (C): 54 mg (2.3) | 36 | 5 |
| Ex. 5A | Monomer (A): 1680 mg (67.8) Polymer (B): 743.1 mg (30.0) Polymerization initiator composition (C): 54 mg (2.2) | 40 | 5 |
| Ex. 6A | Monomer (A): 1680 mg (63.0) Polymer (B): 934 mg (35.0) Polymerization initiator composition (C): 54 mg (2.0) | 92 | 5 |
| Ex. 7A | Monomer (A): 1680 mg (58.1) Polymer (B): 1156 mg (40.0) Polymerization initiator composition (C): 54 mg (1.9) | 164 | 5 |
| Ex. 8A | Monomer (A): 1680 mg (53.3) Polymer (B): 1418.7 mg (45.0) Polymerization initiator composition (C): 54 mg (1.7) | 472 | 5 |
| Ex. 9A | Monomer (A): 1680 mg (48.4) Polymer (B): 1734 mg (50.0) Polymerization initiator composition (C): 54 mg (1.6) | 2560 | 5 |

Preparation of Polymerized and Solidified Film

In a 5 ml sample tube, the polymer (B) was weighed in accordance with a blending ratio described in Examples 10A to 13A of the following Table 2. In the sample tube in which the polymer (B) had been weighed, a mixture of the monomer solution (A) and the polymerization initiator composition (C), which had been prepared in a different 1 ml sample tube in accordance with a blending ratio described in Examples 10A to 13A of the following Table 1 similarly to the above, was introduced, and they were mixed together at 25° C. for about 5 seconds using a glass bar so that the mixture might become homogeneous.

The resulting adhesive composition or wound dressing composition was injected into a syringe and immediately filled in a frame to prepare a sample film in accordance with the following procedure, as illustrated in FIG. 1.

On a glass plate, a sheet of PE Lumirror (trade mark) and a fluororesin frame having a thickness of 0.5 mm (internal size of frame: 25 mm (length)×2 mm (width)) were superposed in this order. In this frame, the adhesive composition or the wound dressing composition prepared was filled. The filling work was carefully carried out so that bubbles should not be formed. After the filling was completed, a sheet of PE Lumirror (trade mark) and a glass plate were further superposed thereon in this order, and the four corners of the outermost two glass plates were fixed with clips. Thereafter, they were allowed to stand for 24 hours at 25° C. (room temperature), and then the film was taken out of the frame. When the resulting film had irregularities on the surfaces, the surfaces were abraded with a waterproof abrasive paper #600 to remove irregularities, whereby a sample film was prepared. The resulting sample film had a size of a length of 25 mm, a width of 2 mm and a thickness of 0.5 mm.

Flexural elastic modulus (test rate: 2 mm/min) and tensile elongation (test rate: 1 mm/min) (SS properties of film) of the sample film were determined by EzTest/CE manufactured by Shimadzu Corporation. The SS property values of the film are each a mean of values measured on four sample film strips. The evaluation results are set forth in Table 2.

TABLE 2

| Adhesive composition or wound dressing composition (part(s) by weight) | Elastic modulus (MPa) | Tensile elongation (%) |
|---|---|---|
| Ex. 10A | Monomer (A): 2637 mg (84.0) Polymer (B): 414 mg (13.2) Polymerization initiator composition (C): 88 mg (2.8) | 310 | 59 |
| Ex. 11A | Monomer (A): 1473 mg (70.8) Polymer (B): 525 mg (25.2) Polymerization initiator composition (C): 83 mg (4.0) | 360 | 60 |
| Ex. 12A | Monomer (A): 586 mg (66.6) Polymer (B): 262 mg (29.7) Polymerization initiator composition (C): 33 mg (3.7) | 420 | 30 |
| Ex. 13A | Monomer (A): 586 mg (51.2) Polymer (B): 525 mg (45.9) Polymerization initiator composition (C): 33 mg (2.9) | 540 | 26 |

Examples 14A to 17A

Evaluation of Adhesive Strength Using Skin of Yucatan Miniature Pig (YMP)

In a 5 ml sample tube, the polymer (B) was weighed in accordance with a blending ratio described in Examples 14A to 17A of the following Table 3. In this sample tube, a mixture of the monomer (A) and the polymerization initiator composition (C), which had been prepared in a different 1 ml sample tube in accordance with a blending ratio described in Examples 14A to 17A of the following Table 3 similarly to the above, was introduced, and they were mixed together at 25° C. for about 5 seconds using a glass bar so that the mixture might become homogeneous.

Figure 2:
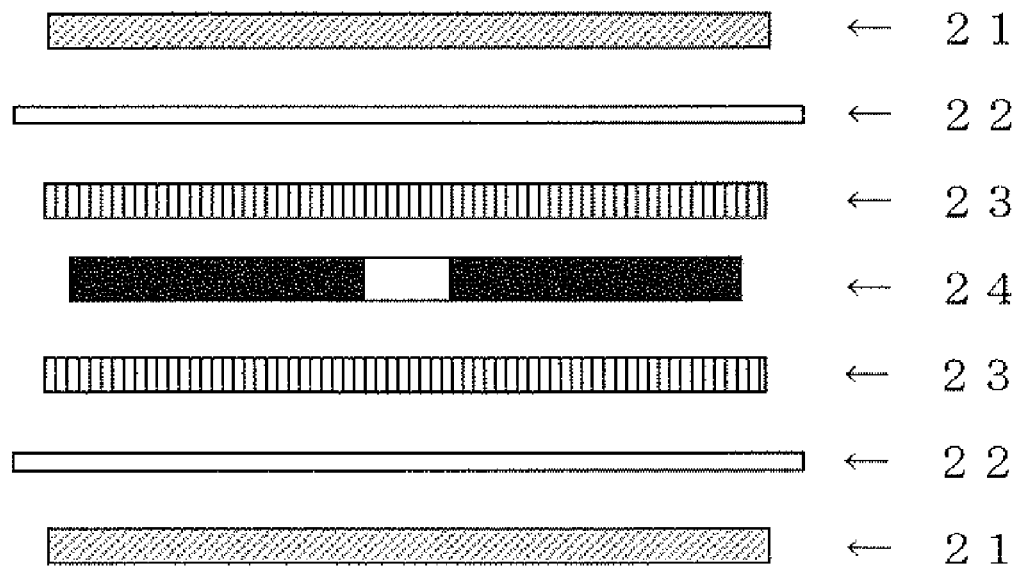
FIG. 2 is a schematic view showing an example of a process for preparing an evaluation sample for evaluating adhesive strength in Examples 14A to 17A of the present invention.
Figure 3:
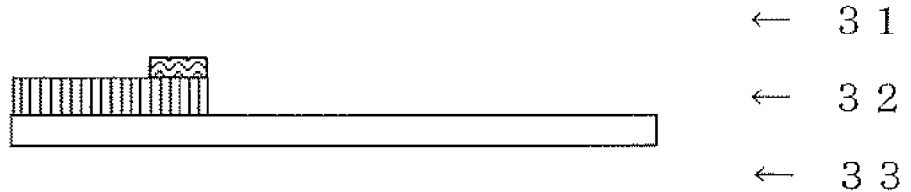
FIG. 3 is a schematic view showing an example of a process for preparing an evaluation sample for evaluating adhesive strength in Examples 1C, 3C, 4C and 17C of the present invention.

The resulting composition was injected into a syringe, and a sample for evaluating adhesive strength was prepared in accordance with the following procedure, as illustrated in FIG. 2. On a glass plate, a sheet of PE lumirror (trade mark), YMP skin of 2 cm×2 cm, from which fat tissue had been cut off and which had been degreased with 70% aqueous ethanol (upper side: outer skin), and a fluororesin sheet frame having a thickness of 0.5 mm, from which a complete round having a diameter of 4.8 mm (area: 18.1 mm$^2$) had been removed, were superposed, and in the fluororesin sheet frame, the adhesive composition or the wound dressing composition shown in Examples 14A to 17A was filled. The filling work was carefully carried out so that bubbles should not be formed. After the filling was completed, YMP skin (lower side: outer skin), a sheet of PE Lumirror (trade mark) and a glass plate were further superposed thereon in this order, and they were allowed to stand for 24 hours at about room temperature of 25° C. under a load of 150 g. Thereafter, the glass plates and the PE lumirror (trade mark) on the both sides were removed to obtain a sample for evaluating adhesive strength. Tension (test rate: 1 mm/min) and adhesive strength of the sample film were determined by EzTest/CE manufactured by Shimadzu Corporation. The value is a mean of values measured on four test strips. The evaluation results measured as above are set forth in Table 3.

TABLE 3

| | Adhesive composition or wound dressing composition (part(s) by weight) | Adhesive strength (kPa) |
|---|---|---|
| Ex. 14A | Monomer (A): 1223 mg (81.5) Polymer (B): 237 mg (15.8) Polymerization initiator composition (C): 41 mg (2.7) | 46 |
| Ex. 15A | Monomer (A): 1071 mg (71.4) Polymer (B): 381 mg (25.4) Polymerization initiator composition (C): 48 mg (3.2) | 91 |
| Ex. 16A | Monomer (A): 885 mg (58.2) Polymer (B): 605 mg (39.8) Polymerization initiator composition (C): 30 mg (2.0) | 114 |
| Ex. 17A | Monomer (A): 763 mg (51.2) Polymer (B): 697 mg (46.8) Polymerization initiator composition (C): 30 mg (2.0) | 93 |

Example 18A

Evaluation of Tissue-Injurious Properties Using Guinea Pig

The back skin of a Hartley type guinea pig of 5 weeks old, whose hair had been clipped and removed, was incised by 3 cm to 4 cm under anesthesia. In a syringe whose discharge opening had been closed with a cap, the polymer (B) was weighed in accordance with a blending ratio described in Example 18A of the following Table 4. Then, the monomer solution (A) and the polymerization initiator composition (C) were mixed in a sample tube in accordance with a blending ratio described in Example 18A similarly to the above, and the mixture was injected into the syringe in which the polymer (B) had been introduced, and they were mixed together at 25° C. Thereafter, the cap of the syringe in which the three components of (A), (B) and (C) had been placed was removed, then a nozzle having an opening of a width of 1 cm and a thickness of 1 mm was fitted, and within 10 seconds, the adhesive composition mixed was extruded through the opening of the syringe nozzle to apply the composition to the incised wound of the guinea pig, said incised wound having been sealed by pressing down it with a finger.

30 minutes, 2 hours, 6 hours, 24 hours, 72 hours and 168 hours after the treatment, properties of the wound, degree of redness and degree of expansion were examined, then the animal was subjected to mercy killing, and the skin of 1 cm×1 cm was cut out from the applied part and fixed in formalin. Thereafter, a tissue slice was prepared in a conventional manner, then subjected to hematoxylin-eosin staining and observed by an optical microscope.

As a result, there was no problem with the properties of the skin, and redness and expansion were not detected. In the observation of the tissue slice, inflammation caused by application of the adhesive composition or the wound dressing composition was not observed, and harmfulness to the skin tissue was not confirmed.

TABLE 4

| | Adhesive composition or wound dressing composition (part(s) by weight) |
|---|---|
| Ex. 18A | Monomer (A): 192 mg (52.6) |
| | Polymer (B): 166 mg (45.5) |
| | Polymerization initiator composition (C): 7 mg (1.9) |

Examples 1B to 7B, Reference Examples 1B to 4B

In the following examples and comparative examples, the same monomer (A), the same polymer (B) and the same polymerization initiator composition (C) as in the above examples were used. As a polymerization inhibitor (D), the following one was used.

Polymerization inhibitor (D): hydroquinone monomethyl ether

In the monomer (A), this polymerization inhibitor was dissolved in an amount described in the following Table 5, Table 6 and Table 7.

Evaluation of Application Properties

In a syringe whose discharge opening had been closed with a cap, 1156 mg (40.0 parts by weight) of the polymer (B) was weighed. Separately, 1680 mg (58.1 parts by weight) of the monomer (A), in which the polymerization inhibitor (D) had been dissolved in an amount (based on the polymer (A)) described in Examples 1B to 3B and Reference Examples 1B and 2B of the following Table 5, and 54 mg (1.9 parts by weight) of the polymerization initiator composition (C) were weighed in a sample tube and mixed together, then the mixture was injected into the syringe in which the polymer (B) had been placed, and they were mixed together at 25° C. Thereafter, the cap of the syringe in which three components of (A), (B) and (C) had been placed was removed, then a nozzle having an opening of a width of 1 cm and a thickness of 1 mm was fitted, and 1 ml of the adhesive composition mixed was applied by 4 cm onto a polyethylene sheet. The application properties were evaluated based on the 5-grade evaluation of 1 to 5. That is to say, a case where the width of the applied composition was not less than 1 cm but less than 1.2 cm was evaluated to be 5; a case where the width of the applied composition was not less than 1.2 cm but less than 1.4 cm was evaluated to be 4; a case where the width of the applied composition was not less than 1.4 cm but less than 1.6 cm was evaluated to be 3; a case where the width of the applied composition was not less than 1.6 cm was evaluated to be 2; and a case where application was impossible was evaluated to be 1. The evaluation results are set forth in Table 5.

Evaluation of Curing Time

In a syringe whose discharge opening had been closed with a cap, 1156 mg (40.0 parts by weight) of the polymer (B) was weighed. Separately, 1680 mg (58.1 parts by weight) of the monomer (A), in which the polymerization inhibitor (D) had been dissolved in an amount (based on the monomer (A)) described in Examples 1B to 3B and Reference Examples 1B and 2B of the following Table 5, and 54 mg (1.9 parts by weight) of the polymerization initiator composition (C) were weighed in a sample tube and mixed together, then the mixture was injected into the syringe in which the polymer (B) had been placed, and they were mixed together at 25° C. Thereafter, the cap of the syringe in which three components of (A), (B) and (C) had been placed was removed, then a nozzle having a width of 1 cm and a thickness of 1 mm was fitted, and 1 ml of the adhesive composition mixed was applied by 4 cm onto a polyethylene sheet. Then, the adhesive composition was held as it was, and a fluororesin bar was touched with the surface of the applied composition to examine the time at the end of which tacking (cobwebbing) stopped. This time was regarded as a curing time. The evaluation results are set forth in Table 5.

TABLE 5

| | Polymerization inhibitor (D) (ppm) | Application properties | Curing time (second(s)) |
|---|---|---|---|
| Ref. Ex. 1B | 0 | 1 | 0 |
| Ex. 1B | 10 | 5 | 5 |
| Ex. 2B | 200 | 5 | 60 |
| Ex. 3B | 5000 | 3 | 750 |
| Ref. Ex. 2B | 10000 | 2 | 1800 |

Evaluation of Storage Stability

In a sample tube of 5 ml, 3000 mg of the monomer (A), in which the polymerization inhibitor (D) had been dissolved in an amount (based on the monomer (A)) described in Examples 4B to 6B and Reference Examples 3B and 4B of the following Table 6, was weighed, and it was stored for 10 days in a constant temperature container at 60° C. After 10 days, the sample tube was opened to examine curing of the contents. The evaluation results are set forth in Table 6.

TABLE 6

| | Polymerization inhibitor (D) (ppm) | Storage stability |
|---|---|---|
| Ref. Ex. 3B | 0 | cured |
| Ex. 4B | 100 | not cured |
| Ex. 5B | 200 | not cured |
| Ex. 6B | 5000 | not cured |
| Ref. Ex. 4B | 10000 | not cured |

Evaluation of Tissue-Injurious Properties Using Guinea Pig

The back skin of a Hartley type guinea pig of 5 weeks old, whose hair had been clipped and removed, was incised by 3 cm to 4 cm under anesthesia. In a syringe having a cap at the luer part, the polymer (B) was weighed in accordance with a blending ratio described in Example 7B of Table 7. In this syringe, the monomer (A) having been mixed with the polymerization inhibitor (D) in a sample tube in accordance with a blending ratio described in Example 7B of Table 7 similarly to the above, and the polymerization initiator composition (C) were injected, and they were mixed together at 25° C. Thereafter, the cap of the syringe was removed, then a nozzle having an opening of a width of 1 cm and a thickness of 1 mm was fitted, and the adhesive composition mixed was applied to the incised part. 30 minutes, 2 hours, 6 hours, 24 hours, 72 hours or 168 hours after the treatment, properties of the skin, presence or absence of redness and presence or absence of expansion were examined, then the animal was subjected to mercy killing, and the skin of 1 cm×1 cm was cut out from the applied part and fixed in formalin. Thereafter, the sample was subjected to H-E staining, and a tissue slice prepared was observed by an optical microscope.

As a result, there was no problem with the properties of the skin, and redness and expansion were not detected. In the observation of the tissue slice, inflammation caused by application of the adhesive composition was not observed, and harmfulness to the skin tissue was not confirmed.

TABLE 7

| Adhesive composition (part(s) by weight) |
| --- |
| Ex. 7B | Monomer (A): 166 mg (45.5)<br>Polymerization inhibitor (D) (based on monomer (A)): 200 ppm<br>Polymer (B): 192 mg (52.6)<br>Polymerization initiator composition (C): 7 mg (1.9) |

Examples 1C to 31C, Comparative Examples 1C to 4C

In the following examples and comparative examples, the same monomer (A) and the same polymerization initiator composition (C) as in the above examples were used. As a polymer (B), a mixture of the aforesaid polymers (b1), (b2) and (b3) in a mixing ratio described in the following Table 8 was used.

Evaluation of Viscosity

In a 5 ml latex-free luer lock syringe (manufactured by HENKE SASS WOLF) having a plastic cap (manufactured by Osaka Chemical Co., Ltd.) at the luer part, the polymer (B) was weighed in accordance with a blending ratio described in Example 1C, Example 3C, Example 4C, Example 9C, Example 10C, Example 15C, Example 17C, Example 19C, Example 22C, Example 23C and Example 27C of the following Tables 8 to 13. In this syringe, the monomer (A) and the polymerization initiator composition (C), which had been mixed together in a 10 ml glass sample tube in accordance with a blending ratio described in the examples similarly to the above, were injected, and the syringe was vigorously shaken with hand at 25° C. for 20 seconds to stir and mix the contents. Thereafter, the cap of the syringe was removed, then an 18 G needle available from Terumo Corporation was fitted, and 60 seconds after the preparation, the viscosity was measured at 35° C. by the use of a rheometer (manufactured by HAAKE, RS150). The viscosity at the time of preparation was not less than 0.4 cp, and it was confirmed that the viscosity increased with time. The evaluation results are set forth in Tables 8 to 15.

Evaluation of Solubility

In a 5 ml latex-free luer lock syringe (manufactured by HENKE SASS WOLF) having a plastic cap (manufactured by Osaka Chemical Co., Ltd.) at the luer part, the polymer (B) was weighed in accordance with a blending ratio described in Examples 1C to 31C and Comparative Examples 1C to 4C of the following Tables 8 to 15. In this syringe, the monomer (A) and the polymerization initiator composition (C), which had been mixed together in a 10 ml glass sample tube in accordance with a blending ratio described in Examples 1C to 31C and Comparative Examples 1C to 4C similarly to the above, were injected, and the syringe was vigorously shaken with hand at 25° C. for 20 seconds to stir and mix the contents. Thereafter, the state of the mixture in the syringe was confirmed by visual observation. A case where a powder of the polymer (B) was not detected was evaluated to be 3; a case where a powder of the polymer (B) was slightly detected was evaluated to be 2; and a case where a powder of the polymer (B) was detected in a large amount was evaluated to be 1. The evaluation results are set forth in Tables 8 to 15.

Evaluation of Application Properties

In a 5 ml syringe (manufactured by HENKE SASS WOLF) having a plastic cap (manufactured by Osaka Chemical Co., Ltd.) at the luer part, the polymer (B) was weighed in accordance with a blending ratio described in Examples 1C to 31C and Comparative Examples 1C to 4C of the following Tables 8 to 15. In this syringe, the monomer (A) and the polymerization initiator composition (C), which had been mixed together in a sample tube in accordance with a blending ratio described in Examples 1C to 31C and Comparative Examples 1C to 4C similarly to the above, were injected, and the syringe was vigorously shaken with hand at 25° C. for 20 seconds to mix the contents. Thereafter, the cap of the syringe was removed, then a nozzle having an opening of a width of 1 cm and a thickness of 1 mm was fitted, and 1 ml of the composition mixed was applied by 4 cm onto a polyethylene sheet. Extrusion from the container was evaluated as follows. That is to say, a case where extrusion could be easily carried out was evaluated to be 3; a case where extrusion could be carried out by applying a pressure with hand was evaluated to be 2; and a case where extrusion was impossible was evaluated to be 1. Spreading of the applied composition was evaluated as follows. That is to say, a case where the width of the applied composition was not less than 1 cm but less than 1.2 cm was evaluated to be 5; a case where the width of the applied composition was not less than 1.2 cm but less than 1.4 cm was evaluated to be 4; a case where the width of the applied composition was not less than 1.4 cm but less than 1.6 cm was evaluated to be 3; a case where the width of the applied composition was not less than 1.6 cm but less than 1.8 cm was evaluated to be 2; a case where the width of the applied composition was not less than 1.8 cm but less than 3 cm was evaluated to be 1; and a case where the width of the applied composition was not less than 3 cm was evaluated to be 0. The evaluation results are set forth in Tables 8 to 15.

Preparation of Polymerized and Solidified Film

In a 5 ml latex-free luer lock syringe (manufactured by HENKE SASS WOLF) having a plastic cap (manufactured by Osaka Chemical Co., Ltd.) at the luer part, the polymer (B) was weighed in accordance with a blending ratio described in Example 1C, Example 3C, Example 4C, Example 10C, Example 15C, Example 17C, Example 19C, Example 22C, Example 23C, Example 27C and Example 28C of the following Tables 8 to 13. In this syringe, the monomer (A) and the polymerization initiator composition (C), which had been mixed together in a sample tube in accordance with a blending ratio described in Example 1C, Example 3C, Example 4C, Example 10C, Example 15C, Example 17C, Example 19C, Example 22C, Example 23C, Example 27C and Example 28C similarly to the above, were injected, and the syringe was vigorously shaken with hand at 25° C. for 20 seconds to mix the contents. The resulting composition was immediately filled in a frame to prepare a sample film in accordance with the following procedure, as illustrated in FIG. 1. On a glass plate, a sheet of PE Lumirror (trade mark) and a fluororesin frame having a thickness of 0.5 mm (internal size of frame: 25 mm (length)×2 mm (width)) were superposed in this order. In this frame, the adhesive composition or the wound dressing composition prepared was filled. The filling work was carefully carried out so that bubbles should not be formed. After the filling was completed, a sheet of PE Lumirror (trade mark) and a glass plate were further superposed thereon in this order, and the four corners of the outermost two glass plates were fixed with clips. Thereafter, they were allowed to stand for 24 hours at 25° C. (room temperature), and then the film was taken out of the frame. When the resulting film had irregularities on the surfaces, the surfaces were abraded with a water proof abrasive paper #600 to remove irregularities, whereby a sample film was prepared. The resulting sample film had a size of a length of 25 mm, a width of 2 mm and a thickness of 0.5 mm.

Flexural elastic modulus (test rate: 2 mm/min) and tensile elongation (test rate: 1 mm/min) of the sample film were determined by an Autograph (EZ-S manufactured by Shimadzu Corporation) The values of the flexural elastic modulus and the tensile elongation of the film are each a mean of values measured on four sample film strips. The evaluation results are set forth in Tables 8 to 13.

Evaluation of Adhesive Strength Using YMP Skin

Test of adhesive strength was carried out based on ASTM F2255-05 using YMP skin (available from Charles River Laboratories Japan, Inc.). That is to say, YMP skin having a thickness of 2 to 3 mm, from which a fat layer had been removed, was cut into a size of 25 mm (width)×20 mm (length), and both surfaces of the skin were wiped with paper. Then, the width of the skin was set to the edges of an acrylic plate having a size of 25 mm (weight)×80 mm (length), and the dermis side of the skin was bonded to the plate with Aron Alpha (trademark, available from TOAGOSEI CO., LTD.) in such a manner that the outer skin was on the upper side. Thereafter, to the skin (outer skin) of an area having a length of not less than 10 mm from the edge of the acrylic plate in the longitudinal direction and to the side surface of the skin, Teflon Grease (trade mark) was applied to define an "adhesive application surface (25 mm (width)×10 mm (length))", whereby an adherend was formed. This adherend was wrapped up in gauze having been soaked with a physiological saline solution, then placed in a closed container and kept warm at 37° C. for 30 minutes. Thereafter, in a 5 ml latex-free luer lock syringe (manufactured by HENKE SASS WOLF) having a plastic cap (manufactured by Osaka Chemical Co., Ltd.) at the luer part, the polymer (B) was weighed in accordance with a blending ratio described in Example 1C, Example 3C, Example 4C and Example 17C of the following Table 8 and Table 11. In this syringe, the monomer (A) and the polymerization initiator composition (C), which had been mixed together in a sample tube in accordance with a blending ratio described in Example 1C, Example 3C, Example 4C and Example 17C similarly to the above, were injected, and the syringe was vigorously shaken with hand at 25° C. for 20 seconds to mix the contents, whereby an adhesive composition or a wound dressing composition was prepared. The adhesive composition or the wound dressing composition was applied to the adhesive application surface (25 mm×10 mm). Two of such samples were prepared, and these were laid one upon the other in such a manner that the adhesive applied surfaces faced each other, and allowed to stand still for 1 hour under a load of 140 g. Thereafter, the resulting sample was wrapped up in gauze having been soaked with a physiological saline solution, placed in a container and allowed to stand still at 37° C. for 24 hours to prepare an adhesive strength evaluation sample.

The evaluation sample was subjected to tensile test using an Autograph (EZ-S manufactured by Shimadzu Corporation) at a test rate of 5 mm/min. A mean of values measured on four test strips was determined as adhesive strength. The evaluation results are set forth in Table 8 and Table 11.

Overall Evaluation

A case where the points of solubility and application properties (extrusion from container, spreading of applied composition) were each 3 or more was evaluated to be AA; a case where the points of solubility and application properties (extrusion from container, spreading of applied composition) were each 2 or more was evaluated to be A; a case where the points of solubility and application properties (extrusion from container) were each 2 or more and the point of application properties (spreading of applied composition) was 1 or more was evaluated to be B; and any of a case where the point of solubility was 1, a case where the point of application properties (extrusion from container) was 1, and a case where the point of application properties (spreading of applied composition) was 0 was evaluated to be C. The evaluation results are set forth in Tables 8 to 15.

TABLE 8

| | Adhesive composition or wound dressing composition (part(s) by weight) | Viscosity 60 seconds after mixing (cp) | Solubility | Application properties | | Mechanical properties | | | Overall evaluation |
|---|---|---|---|---|---|---|---|---|---|
| | | | | Extrusion from container | Spreading of applied composition | Elastic modulus (MPa) | Tensile elongation (%) | Adhesive strength (MPa) | |
| Ex. 1C | Monomer (A): 560 mg (80.0) Polymer (B): 105 mg (15.0) (b1): 25.0% (b2): 62.5% (b3): 12.5% Polymerization initiator composition (C): 35 mg (5.0) | 100 | 3 | 3 | 1 | 416 | 74 | 42 | B |
| Ex. 2C | Monomer (A): 560 mg (80.0) Polymer (B): 105 mg (15.0) (b1): 75.0% | | 3 | 3 | 2 | | | | A |

TABLE 8-continued

| | Adhesive composition or wound dressing composition (part(s) by weight) | Viscosity 60 seconds after mixing (cp) | Solubility | Application properties | | Mechanical properties | | | Overall evaluation |
|---|---|---|---|---|---|---|---|---|---|
| | | | | Extrusion from container | Spreading of applied composition | Elastic modulus (MPa) | Tensile elongation (%) | Adhesive strength (MPa) | |
| Ex. 3C | (b2): 0%<br>(b3): 25.0%<br>Polymerization initiator composition (C): 35 mg (5.0)<br>Monomer (A): 560 mg (75.3)<br>Polymer (B): 149 mg (20.0)<br>(b1): 25.0%<br>(b2): 62.5%<br>(b3): 12.5%<br>Polymerization initiator composition (C): 35 mg (4.7) | 160 | 3 | 3 | 2 | 430 | 80 | 50 | A |
| Ex. 4C | Monomer (A): 560 mg (70.6)<br>Polymer (B): 198 mg (25.0)<br>(b1): 25.0%<br>(b2): 62.5%<br>(b3): 12.5%<br>Polymerization initiator composition (C): 35 mg (4.4) | 180 | 3 | 3 | 2 | 450 | 50 | 73 | A |
| Ex. 5C | Monomer (A): 560 mg (70.6)<br>Polymer (B): 198 mg (25.0)<br>(b1): 50.0%<br>(b2): 50.5%<br>(b3): 0%<br>Polymerization initiator composition (C): 35 mg (4.4) | | 3 | 3 | 3 | | | | AA |

TABLE 9

| | Adhesive composition or wound dressing composition (part(s) by weight) | Viscosity 60 seconds after mixing (cp) | Solubility | Application properties | | Mechanical properties | | | Overall evaluation |
|---|---|---|---|---|---|---|---|---|---|
| | | | | Extrusion from container | Spreading of applied composition | Elastic modulus (MPa) | Tensile elongation (%) | Adhesive strength (MPa) | |
| Ex. 6C | Monomer (A): 560 mg (70.6)<br>Polymer (B): 198 mg (25.0)<br>(b1): 87.5%<br>(b2): 0%<br>(b3): 12.5%<br>Polymerization initiator composition (C): 35 mg (4.4) | | 3 | 3 | 5 | | | | AA |
| Ex. 7C | Monomer (A): 560 mg (65.9)<br>Polymer (B): 255 mg (30.0)<br>(b1): 12.5%<br>(b2): 87.5%<br>(b3): 0% | | 3 | 3 | 3 | | | | AA |

TABLE 9-continued

| | Adhesive composition or wound dressing composition (part(s) by weight) | Viscosity 60 seconds after mixing (cp) | Solubility | Application properties | | Mechanical properties | | | Overall evaluation |
|---|---|---|---|---|---|---|---|---|---|
| | | | | Extrusion from container | Spreading of applied composition | Elastic modulus (MPa) | Tensile elongation (%) | Adhesive strength (MPa) | |
| Ex. 8C | Monomer (A): 560 mg (65.9) Polymer (B): 255 mg (30.0) (b1): 12.5% (b2): 0% (b3): 87.5% Polymerization initiator composition (C): 35 mg (4.1) | | 3 | 3 | 2 | | | | A |
| Ex. 9C | Monomer (A): 560 mg (65.9) Polymer (B): 255 mg (30.0) (b1): 25.0% (b2): 75.0% (b3): 0% Polymerization initiator composition (C): 35 mg (4.1) | 3900 | 3 | 3 | 4 | | | | AA |
| Ex. 10C | Monomer (A): 560 mg (65.9) Polymer (B): 255 mg (30.0) (b1): 50.0% (b2): 0% (b3): 50.0% Polymerization initiator composition (C): 35 mg (4.1) | 4600 | 3 | 3 | 4 | 700 | 14 | | AA |

TABLE 10

| | Adhesive composition or wound dressing composition (part(s) by weight) | Viscosity 60 seconds after mixing (cp) | Solubility | Application properties | | Mechanical properties | | | Overall evaluation |
|---|---|---|---|---|---|---|---|---|---|
| | | | | Extrusion from container | Spreading of applied composition | Elastic modulus (MPa) | Tensile elongation (%) | Adhesive strength (MPa) | |
| Ex. 11C | Monomer (A): 560 mg (65.9) Polymer (B): 255 mg (30.0) (b1): 75.0% (b2): 25.0% (b3): 0% Polymerization initiator composition (C): 35 mg (4.1) | | 2 | 3 | 5 | | | | A |
| Ex. 12C | Monomer (A): 560 mg (56.5) Polymer (B): 397 mg (40.0) (b1): 0% (b2): 100% (b3): 0% | | 3 | 3 | 2 | | | | A |

TABLE 10-continued

| | Adhesive composition or wound dressing composition (part(s) by weight) | Viscosity 60 seconds after mixing (cp) | Solubility | Application properties | | Mechanical properties | | | Overall evaluation |
|---|---|---|---|---|---|---|---|---|---|
| | | | | Extrusion from container | Spreading of applied composition | Elastic modulus (MPa) | Tensile elongation (%) | Adhesive strength (MPa) | |
| | Polymerization initiator composition (C): 35 mg (3.5) | | | | | | | | |
| Ex. 13C | Monomer (A): 560 mg (56.5) Polymer (B): 397 mg (40.0) (b1): 0% (b2): 0% (b3): 100% Polymerization initiator composition (C): 35 mg (3.5) | | 3 | 3 | 1 | | | | B |
| Ex. 14C | Monomer (A): 560 mg (56.5) Polymer (B): 397 mg (40.0) (b1): 12.5% (b2): 87.5% (b3): 0% Polymerization initiator composition (C): 35 mg (3.5) | | 3 | 3 | 4 | | | | AA |
| Ex. 15C | Monomer (A): 560 mg (56.5) Polymer (B): 397 mg (40.0) (b1): 50.0% (b2): 0% (b3): 50.0% Polymerization initiator composition (C): 35 mg (3.5) | 12800 | 3 | 3 | 5 | 440 | 68 | | AA |

TABLE 11

| | Adhesive composition or wound dressing composition (part(s) by weight) | Viscosity 60 seconds after mixing (cp) | Solubility | Application properties | | Mechanical properties | | | Overall evaluation |
|---|---|---|---|---|---|---|---|---|---|
| | | | | Extrusion from container | Spreading of applied composition | Elastic modulus (MPa) | Tensile elongation (%) | Adhesive strength (MPa) | |
| Ex. 16C | Monomer (A): 560 mg (56.5) Polymer (B): 397 mg (40.0) (b1): 75.0% (b2): 25.0% (b3): 0% Polymerization initiator composition (C): 35 mg (3.5) | | 2 | 2 | 5 | | | | A |
| Ex. 17C | Monomer (A): 560 mg (51.8) Polymer (B): 487 mg (45.0) (b1): 25.0% (b2): 62.5% (b3): 12.5% | 11000 | 3 | 3 | 5 | 530 | 35 | 83 | AA |

TABLE 11-continued

| | Adhesive composition or wound dressing composition (part(s) by weight) | Viscosity 60 seconds after mixing (cp) | Solubility | Application properties | | Mechanical properties | | | Overall evaluation |
|---|---|---|---|---|---|---|---|---|---|
| | | | | Extrusion from container | Spreading of applied composition | Elastic modulus (MPa) | Tensile elongation (%) | Adhesive strength (MPa) | |
| | Polymerization initiator composition (C): 35 mg (3.2) | | | | | | | | |
| Ex. 18C | Monomer (A): 560 mg (51.8) Polymer (B): 487 mg (45.0) (b1): 37.5% (b2): 0% (b3): 62.5% Polymerization initiator composition (C): 35 mg (3.2) | | 3 | 2 | 5 | | | | A |
| Ex. 19C | Monomer (A): 560 mg (47.1) Polymer (B): 595 mg (50.0) (b1): 0% (b2): 100% (b3): 0% Polymerization initiator composition (C): 35 mg (2.9) | 20800 | 3 | 3 | 5 | 540 | 12 | | AA |
| Ex. 20C | Monomer (A): 560 mg (47.1) Polymer (B): 595 mg (50.0) (b1): 0% (b2): 50.0% (b3): 50.0% Polymerization initiator composition (C): 35 mg (2.9) | | 3 | 3 | 3 | | | | AA |

TABLE 12

| | Adhesive composition or wound dressing composition (part(s) by weight) | Viscosity 60 seconds after mixing (cp) | Solubility | Application properties | | Mechanical properties | | | Overall evaluation |
|---|---|---|---|---|---|---|---|---|---|
| | | | | Extrusion from container | Spreading of applied composition | Elastic modulus (MPa) | Tensile elongation (%) | Adhesive strength (MPa) | |
| Ex. 21C | Monomer (A): 560 mg (47.1) Polymer (B): 595 mg (50.0) (b1): 0% (b2): 0% (b3): 100% Polymerization initiator composition (C): 35 mg (2.9) | | 3 | 3 | 2 | | | | A |
| Ex. 22C | Monomer (A): 560 mg (47.1) Polymer (B): 595 mg (50.0) (b1): 25.0% (b2): 12.5% (b3): 62.5% | 119000 | 3 | 3 | 5 | 490 | 16 | | AA |

TABLE 12-continued

| | Adhesive composition or wound dressing composition (part(s) by weight) | Viscosity 60 seconds after mixing (cp) | Solubility | Application properties | | Mechanical properties | | | Overall evaluation |
|---|---|---|---|---|---|---|---|---|---|
| | | | | Extrusion from container | Spreading of applied composition | Elastic modulus (MPa) | Tensile elongation (%) | Adhesive strength (MPa) | |
| Ex. 23C | Monomer (A): 560 mg (47.1) Polymer (B): 595 mg (50.0) (b1): 25.0% (b2): 0% (b3): 75.0% Polymerization initiator composition (C): 35 mg (2.9) | 41700 | 3 | 3 | 5 | 590 | 23 | | AA |
| Ex. 24C | Monomer (A): 560 mg (47.1) Polymer (B): 595 mg (50.0) (b1): 50.0% (b2): 50.0% (b3): 0% Polymerization initiator composition (C): 35 mg (2.9) | | 3 | 2 | 5 | | | | A |
| Ex. 25C | Monomer (A): 560 mg (47.1) Polymer (B): 595 mg (50.0) (b1): 75.0% (b2): 0% (b3): 25.0% Polymerization initiator composition (C): 35 mg (2.9) | | 3 | 2 | 2 | | | | A |

TABLE 13

| | Adhesive composition or wound dressing composition (part(s) by weight) | Viscosity 60 seconds after mixing (cp) | Solubility | Application properties | | Mechanical properties | | | Overall evaluation |
|---|---|---|---|---|---|---|---|---|---|
| | | | | Extrusion from container | Spreading of applied composition | Elastic modulus (MPa) | Tensile elongation (%) | Adhesive strength (MPa) | |
| Ex. 26C | Monomer (A): 560 mg (42.4) Polymer (B): 727 mg (55.0) (b1): 25.0% (b2): 75.0% (b3): 0% Polymerization initiator composition (C): 35 mg (2.6) | | 2 | 2 | 5 | | | | A |
| Ex. 27C | Monomer (A): 560 mg (37.6) Polymer (B): 893 mg (60.0) (b1): 0% (b2): 100% (b3): 0% | 390000 | 3 | 3 | 5 | 530 | 19 | | AA |

TABLE 13-continued

| Adhesive composition or wound dressing composition (part(s) by weight) | Viscosity 60 seconds after mixing (cp) | Solubility | Application properties | | Mechanical properties | | | Overall evaluation |
|---|---|---|---|---|---|---|---|---|
| | | | Extrusion from container | Spreading of applied composition | Elastic modulus (MPa) | Tensile elongation (%) | Adhesive strength (MPa) | |
| Ex. 28C | Monomer (A): 560 mg (37.6) Polymer (B): 893 mg (60.0) (b1): 0% (b2): 33.3% (b3): 66.7% Polymerization initiator composition (C): 35 mg (2.4) | | 3 | 3 | 5 | 560 | 10 | | AA |
| Ex. 29C | Monomer (A): 560 mg (37.6) Polymer (B): 893 mg (60.0) (b1): 0% (b2): 16.7% (b3): 83.3% Polymerization initiator composition (C): 35 mg (2.4) | | 3 | 3 | 2 | | | | A |
| Ex. 30C | Monomer (A): 560 mg (32.9) Polymer (B): 1105 mg (65.0) (b1): 0% (b2): 100% (b3): 0% Polymerization initiator composition (C): 35 mg (2.1) | | 3 | 2 | 5 | | | | A |

TABLE 14

| Adhesive composition or wound dressing composition (part(s) by weight) | Viscosity 60 seconds after mixing (cp) | Solubility | Application properties | | Mechanical properties | | | Overall evaluation |
|---|---|---|---|---|---|---|---|---|
| | | | Extrusion from container | Spreading of applied composition | Elastic modulus (MPa) | Tensile elongation (%) | Adhesive strength (MPa) | |
| Ex. 31C | Monomer (A): 560 mg (32.9) Polymer (B): 1105 mg (65.0) (b1): 0% (b2): 0% (b3): 100% Polymerization initiator composition (C): 35 mg (2.1) | | 3 | 2 | 5 | | | | A |

TABLE 15

| Adhesive composition or wound dressing composition (part(s) by weight) | Viscosity 60 seconds after mixing (cp) | Solubility | Application properties Extrusion from container | Application properties Spreading of applied composition | Mechanical properties Elastic modulus (MPa) | Mechanical properties Tensile elongation (%) | Mechanical properties Adhesive strength (MPa) | Overall evaluation |
|---|---|---|---|---|---|---|---|---|
| Comp. Ex. 1C | Monomer (A): 560 mg (84.7) Polymer (B): 66 mg (10.0) (b1): 25.0% (b2): 62.5% (b3): 12.5% Polymerization initiator composition (C): 35 mg (5.3) | 3 | 3 | 0 | | | | C |
| Comp. Ex. 2C | Monomer (A): 560 mg (65.9) Polymer (B): 255 mg (30.0) (b1): 0% (b2): 100% (b3): 0% Polymerization initiator composition (C): 35 mg (4.1) | 3 | 3 | 0 | | | | C |
| Comp. Ex. 3C | Monomer (A): 560 mg (47.1) Polymer (B): 595 mg (50.0) (b1): 75.0% (b2): 25.0% (b3): 0% Polymerization initiator composition (C): 35 mg (2.9) | 1 | 2 | 5 | | | | C |
| Comp. Ex. 4C | Monomer (A): 560 mg (37.6) Polymer (B): 893 mg (60.0) (b1): 25.0% (b2): 62.5% (b3): 12.5% Polymerization initiator composition (C): 35 mg (2.4) | 1 | 2 | 5 | | | | C |

Examples 32C to 34C, Comparative Example 5C

Evaluation of Tissue-Injurious Properties Using Rat

A male Crl:CD (SD) rat (SPF, Charles river Laboratories Japan, Ltd.) of 11 weeks old, whose hair on the back had been clipped by electric hair clippers, was anesthetized with pentobarbital sodium, and the skin was sterilized by alcoholic cotton. In a 5 ml latex-free luer lock syringe (manufactured by HENKE SASS WOLF) having a plastic cap (manufactured by Osaka Chemical Co., Ltd.) at the luer part, the polymer (B) was weighed in accordance with a blending ratio described in Examples 32C to 34C of Table 16. In this syringe, the monomer (A) and the polymerization initiator composition (C), which had been mixed together in a 10 ml glass sample tube in accordance with a blending ratio described in Examples 32C to 34C of Table 16 similarly to the above, were injected, and the syringe was vigorously shaken with hand at 25° C. for 20 seconds to stir and mix the contents. After the mixing, the plastic cap was removed, then a needle (18 G) was fitted, and air was sufficiently removed from the syringe, followed by administration of 400 µl under the skin (between dermis and subcutaneous fat) of the back. As a comparative example, 400 µl of a cyanoacrylate-based skin adhesive Dermabond (trade mark, available from Johnson & Johnson K.K.) was administered. As a negative control, 400 µl of a physiological saline solution was administered.

72 hours or 168 hours after the administration, the rat was subjected to mercy killing, then the skin of the back at the subcutaneous administration part was extracted as it was without clipping the hair, and it was fixed in formalin. After the fixation, a paraffin embedded block was prepared, and it was subjected to hematoxylin-eosin (H-E) staining (lymphocyte staining), Congo red staining (eosinophil staining) and toluidine blue staining (mast cell staining), followed by microscopic observation. The tissue-injurious properties were evaluated by scores on the pathological findings (0: no findings, 1: soft, 2: mild, 3: moderate, 4: severe). The evaluation results are set forth in Table 16.

As a result, it was confirmed that moderate inflammation occurred by the contact of Dermabond (trade mark) with the subcutaneous tissue, but in the case of the adhesive composition or the wound dressing composition, inflammation was rarely observed. From this, it was confirmed that the composition had high safety as an adhesive for skins or a wound dressing.

TABLE 16

| Adhesive composition or wound dressing composition (part(s) by weight) | H-E staining 72 hr | H-E staining 168 hr | Congo red staining 72 hr | Congo red staining 168 hr | toluidine blue staining 72 hr | toluidine blue staining 168 hr |
|---|---|---|---|---|---|---|
| Ex. 32C — Monomer (A): 560 mg (75.3); Polymer (B): 149 mg (20.0); (b1): 25.0%; (b2): 62.5%; (b3): 12.5%; Polymerization initiator composition (C): 35 mg (4.7) | 2 | 2 | 2 | 1 | 2 | 2 |
| Ex. 33C — Monomer (A): 560 mg (65.9); Polymer (B): 255 mg (30.0); (b1): 25.0%; (b2): 62.5%; (b3): 12.5%; Polymerization initiator composition (C): 35 mg (4.1) | 2 | 2 | 1 | 1 | 2 | 2 |
| Ex. 34C — Monomer (A): 560 mg (56.5); Polymer (B): 397 mg (40.0); (b1): 25.0%; (b2): 62.5%; (b3): 12.5%; Polymerization initiator composition (C): 35 mg (3.5) | 1 | 2 | 1 | 1 | 2 | 2 |
| Comp. Ex. 5C — Dermabond | 3 | 3 | 3 | 3 | 2 | 2 |
| Negative control — Physiological saline solution | 1 | 1 | 1 | 1 | 2 | 2 |

Confirmation of Healing of Incised Part Using Rat

A male SD rat of 5 weeks old was anesthetized with Somnopentyl and then subjected to hair shearing. A penetrating skin cut wound of 30 mm was made at the position of 5 mm from the xiphoid process toward the tail. In a 5 ml latex-free luer lock syringe (manufactured by HENKE SASS WOLF) having a plastic cap (manufactured by Osaka Chemical Co., Ltd.) at the luer part, the polymer (B) was weighed in accordance with a blending ratio described in Example 34C of Table 16. In this syringe, the monomer (A) and the polymerization initiator composition (C), which had been mixed together in a 10 ml glass sample tube in accordance with a blending ratio described in Example 34C of Table 16 similarly to the above, were injected, and the syringe was vigorously shaken with hand at 25° C. for 20 seconds to stir and mix the contents. Thereafter, the plastic cap was removed, then a nozzle having an opening of a width of 1 cm and a thickness of 1 mm was fitted. Bleeding at the cut wound was stopped using gauze, and then, with tightly pressing down the joined surface, 500 µl of the adhesive was applied thereto. 1 week, 2 weeks or 3 months after the treatment, the rat was subjected to mercy killing, and the abdominal tissue (skin and subcutaneous tissue) having a size of 3 cm (length)×2 cm (width) was extracted and fixed in formalin. After the fixation, a paraffin embedded block was prepared, and it was subjected to hematoxylin-eosin (H-E) staining, followed by evaluation of the degree of healing by microscopic observation.

As a result, it was confirmed that the incised part where the adhesive for skins or the wound dressing composition had been applied did not differ from a non-incised tissue, and it had healed sufficiently.

REFERENCE SIGNS LIST

11: glass plate, 12: Lumirror (trade mark), 13: fluororesin frame (the central white part indicates a space of 25 mm (length)×2 mm (width), and this part is filled with the adhesive composition or the wound dressing composition.)
21: glass plate, 22: Lumirror (trade mark), 23: YMP skin (outer skin: lower side), 24: fluororesin frame (the central white part indicates a complete round having a diameter of 4.8 mm, and this part is filled with the adhesive composition or the wound dressing composition.)
31: Teflon Grease applied part, 32: YMP skin (outer skin: upper side), 33: acrylic plate

The invention claimed is:

1. An adhesive composition for soft tissues, an adhesive composition for wound dressing or a wound dressing composition, comprising a monomer (A), a (meth)acrylate uncrosslinked polymer (B) and a polymerization initiator composition (C) containing an organoboron compound, and
    having a viscosity of 0.4 to 75,000 cp within 30 seconds after mixing of the components (A), (B) and (C),
    wherein the polymer (B) is a polymer mixture which comprises polymer particles (b1) having a weight-average molecular weight of $30\times10^4$ to $60\times10^4$ and a specific surface area of 1.5 to 4.5 ($m^2/g$), polymer particles (b2) having a weight-average molecular weight of $5\times10^4$ to $20\times10^4$ and a specific surface area of 0.51 to 1.2 ($m^2/g$) and polymer particles (b3) having a weight-average molecular weight of $5\times10^4$ to $20\times10^4$ and a specific surface area of 0.1 to 0.5 ($m^2/g$), contains the polymer particles (b1) in an amount of 10 to 60% by weight, and contains the polymer particles (b2) and the polymer particles (b3) in the total amount of not less than 2% by weight based on the total weight of the polymer particles (b1), (b2) and (b3), with the proviso that the total amount of the polymer particles (b1), (b2) and (b3) is 100% by weight, and wherein the amount of the component (B) is in the range of 28 to 55 parts by weight, based on 100 parts by weight of the total amount of the monomer (A), the polymer (B) and the polymerization initiator composition (C).

2. The adhesive composition for soft tissues, the adhesive composition for wound dressing or the wound dressing composition as claimed in claim 1, wherein a film, which is obtained from said adhesive composition or wound dressing composition, is given 24 hours after the preparation of the composition and has a thickness of not less than 0.1 μm, a length of not less than 25 mm and a width of not less than 2 mm, has a flexural elastic modulus, as measured under the conditions of a test rate of 2 mm/min, of not more than 750 MPa and a tensile elongation, as measured under the conditions of a test rate of 1 mm/min, of not less than 5%.

3. The adhesive composition for soft tissues, the adhesive composition for wound dressing or the wound dressing composition as claimed in claim 1, which further comprises a polymerization inhibitor (D).

4. The adhesive composition for soft tissues, the adhesive composition for wound dressing or the wound dressing composition as claimed in claim 3, wherein the content of the polymerization inhibitor (D) is in the range of 10 to 5000 ppm based on the monomer (A).

5. The adhesive composition for soft tissues, the adhesive composition for wound dressing or the wound dressing composition as claimed in claim 3, wherein the polymerization inhibitor (D) is at least one substance selected from hydroquinone, dibutylhydroquinone, hydroquinone monomethyl ether, 2,6-di-tert-butylphenol, 2,6-di-tert-butyl-p-cresol, catechol, pyrogallol, benzoquinone, 2-hydroxybenzoquinone, p-methoxyphenol, t-butylcatechol, butylated hydroxyanisole, butylated hydroxytoluene and t-butylhydroquinone.

6. The adhesive composition for soft tissues, the adhesive composition for wound dressing or the wound dressing composition as claimed in claim 1, which further comprises an ultraviolet light absorber.

7. The adhesive composition for soft tissues, the adhesive composition for wound dressing or the wound dressing composition as claimed in claim 1, which further comprises a plasticizer.

8. The adhesive composition for soft tissues, the adhesive composition for wound dressing or the wound dressing composition as claimed in claim 1, which further comprises at least one substance selected from:

anti-infectious agents, antibiotics, antibacterial agents, anti-virus agents, analgesics, compositions of analgesics, anorectic drugs, antihelmintic drugs, antiarthritic agents, antiasthmatic drugs, anticonvulsants, antidepressants, antidiuretics, antidiarrheal agents, antihistamine drugs, anti-inflammatory drugs, antimigraine drugs, antiemetic agents, antineoplastic drugs, antiparkinsonian agents, antipruritic drugs, antipsychotics, antipyretic drugs, antispasmodic drugs, anticholinergic agents, sympathomimetic agents, cardiovascular drugs, antiarrhythmic drugs, antihypertensive drugs, diuretics, vasodilators, immunosuppressant drugs, muscle-relaxant drugs, parasympatholytic drugs, stimulants, sedative drugs, tranquilizers, cholinergic agents, chemotherapeutic drugs, radio pharmaceuticals, bone inductive drugs, heparin neutralizer agents of static bladder, procoagulants, hemostatic agents, xanthine derivatives, hormones, proteins of natural origin or proteins synthesized by genetic engineering, polysaccharides, glycoproteins, lipoproteins, oligonucleotides, antibody, antigen, vasopressin, vasopressin analogs, epinephrine, selectin, clot promoting toxicants, plasminogen activating factor inhibitors, platelet activators, synthetic peptides having hemostatic action, and perfumes, such as orange oil, grapefruit oil, lemon oil, lime oil, clove oil, wintergreen oil, peppermint oil, peppermint spirit, banana distillate, cucumber distillate, honey distillate, rose water, menthol, anethole, alkyl salicylate, benzaldehyde, monosodium glutamate, ethylvanillin, thymol and vanillin.

9. An adhesive kit for soft tissues, an adhesive agent kit for wound dressing or a wound dressing kit, having members in which the components of the monomer (A), the polymer (B) and the polymerization initiator composition (C) containing an organoboron compound, which are contained in the adhesive composition for soft tissues, the adhesive composition for wound dressing or the wound dressing composition as claimed in claim 1, are encased in two or more divided groups in an optional combination.

10. The adhesive kit for soft tissues, the adhesive kit for wound dressing or the wound dressing kit as claimed in claim 9, which has constitution in which the monomer (A), the polymer (B) and the polymerization initiator composition (C) are each independently encased, and the monomer (A) is first mixed with the polymerization initiator composition (C) containing an organoboron compound and subsequently mixed with the polymer (B).

11. An adhesive kit for soft tissues, an adhesive agent kit for wound dressing or a wound dressing kit, having members in which the components of the monomer (A), the (meth)acrylate polymer (B), the polymerization initiator composition (C) containing an organoboron compound and the polymerization inhibitor (D), which are contained in the adhesive composition for soft tissues, the adhesive composition for wound dressing or the wound dressing composition as claimed in claim 3, are encased in two or more divided groups in an optional combination.

12. The adhesive kit for soft tissues, the adhesive kit for wound dressing or the wound dressing kit as claimed in claim 11, which has constitution in which a mixture of the monomer (A) and the polymerization inhibitor (D), the polymer (B) and the polymerization initiator composition (C) are each independently encased, and the mixture of the monomer (A) and the polymerization inhibitor (D) is first mixed with the polymerization initiator composition (C) containing an organoboron compound and subsequently mixed with the polymer (B).

13. The adhesive kit for soft tissues, the adhesive kit for wound dressing or the wound dressing kit as claimed in claim 9, which includes a jig that is used for applying a composition obtained by mixing adhesive components or wound dressing components containing the components (A), (B) and (C).

14. The adhesive kit for soft tissues, the adhesive kit for wound dressing or the wound dressing kit as claimed in claim 13, wherein the jig is at least one jig selected from a brush, a fiber ball, a cloth, a sponge ball and a piece of sponge.

15. The adhesive kit for soft tissues, the adhesive kit for wound dressing or the wound dressing kit as claimed in claim 9, which further contains an aqueous solution for adhesion pretreatment containing 1 to 15% by weight of citric acid and 1 to 5% by weight of iron(III) chloride.

16. The adhesive kit for soft tissues, the adhesive kit for wound dressing or the wound dressing kit as claimed in claim 11, which includes a jig that is used for applying a composition obtained by mixing adhesive components or wound dressing components containing the components (A), (B), (C) and (D).

17. The adhesive kit for soft tissues, the adhesive kit for wound dressing or the wound dressing kit as claimed in claim 16, wherein the jig is at least one jig selected from a brush, a fiber ball, a cloth, a sponge ball and a piece of sponge.

18. The adhesive kit for soft tissues, the adhesive kit for wound dressing or the wound dressing kit as claimed in claim 11, which further contains an aqueous solution for adhesion pretreatment containing 1 to 15% by weight of citric acid and 1 to 5% by weight of iron(III) chloride.

19. The adhesive composition for soft tissues, the adhesive composition for wound dressing or the wound dressing composition as claimed in claim 1, which has a viscosity of 100 to 1,000,000 cp 60 seconds after mixing of the components (A), (B) and (C).

* * * * *